US011759803B2

(12) United States Patent
Asami et al.

(10) Patent No.: US 11,759,803 B2
(45) Date of Patent: *Sep. 19, 2023

(54) METHOD FOR PRODUCING WEARABLE COATING

(71) Applicant: KAO CORPORATION, Tokyo (JP)

(72) Inventors: Nobuyuki Asami, Tokyo (JP); Asuka Imai, Cincinnati, OH (US); Michael Rosner, Los Angeles, CA (US)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/683,840

(22) Filed: Mar. 1, 2022

(65) Prior Publication Data

US 2022/0305507 A1   Sep. 29, 2022

Related U.S. Application Data

(62) Division of application No. 16/527,925, filed on Jul. 31, 2019, now Pat. No. 11,338,308.

(60) Provisional application No. 62/716,537, filed on Aug. 9, 2018.

(51) Int. Cl.

| B05B 5/16 | (2006.01) |
|---|---|
| A45D 34/04 | (2006.01) |
| B05B 5/025 | (2006.01) |
| A61K 8/02 | (2006.01) |
| A61K 8/81 | (2006.01) |
| A61K 8/31 | (2006.01) |
| A61K 8/34 | (2006.01) |
| A61K 8/35 | (2006.01) |
| A61K 8/04 | (2006.01) |

(52) U.S. Cl.
CPC ............ B05B 5/1675 (2013.01); A45D 34/04 (2013.01); B05B 5/0255 (2013.01); A61K 8/027 (2013.01); A61K 8/04 (2013.01); A61K 8/31 (2013.01); A61K 8/345 (2013.01); A61K 8/35 (2013.01); A61K 8/8129 (2013.01)

(58) Field of Classification Search
None
See application file for complete search history.

(56) References Cited

U.S. PATENT DOCUMENTS

| 6,468,508 | B1 | 10/2002 | Laughlin |
|---|---|---|---|
| 6,514,504 | B1 | 2/2003 | Yen |
| 2008/0045553 | A1 | 2/2008 | Wilson |
| 2013/0034513 | A1 | 2/2013 | Samain |
| 2014/0328776 | A1 | 11/2014 | Dong |
| 2014/0345639 | A1 | 11/2014 | Samain et al. |
| 2018/0317627 | A1 | 11/2018 | Fukuda et al. |
| 2018/0325789 | A1 | 11/2018 | Takemoto |
| 2019/0059551 | A1 | 2/2019 | Amari et al. |

FOREIGN PATENT DOCUMENTS

| AU | 2016340485 B2 | 6/2018 |
|---|---|---|
| CA | 3001821 | 4/2017 |
| CN | 103025784 A | 4/2013 |
| CN | 108135788 A | 6/2018 |
| EP | 1 348 426 A1 | 10/2003 |
| JP | 2007-538010 | 12/2007 |
| JP | 2011-246672 A | 12/2011 |
| JP | 2015-000872 | 1/2015 |
| JP | 2016-027027 | 2/2016 |
| JP | 2017-078063 | 4/2017 |
| JP | 2017-095449 | 6/2017 |
| JP | 2018-053001 | 4/2018 |
| TW | 201729785 A | 9/2017 |
| TW | 201729786 A | 9/2017 |
| WO | WO 02-009653 | 2/2002 |
| WO | WO 2007078486 | 7/2007 |
| WO | WO 2017/069080 A1 | 4/2017 |
| WO | WO 2017-083398 | 5/2017 |
| WO | WO 2018/097202 A1 | 5/2018 |

OTHER PUBLICATIONS

Database GNPD [Online] MINTEL; Jan. 26, 2016, anonymous: "Super Sealer Mattifying Setting Spray", XP055904532, 4 pages.
Database GNPD [Online] MINTEL; Nov. 9, 2006, anonymous: "Magic Sealer", XP055904590, 2 pages.
International Search Report and Written Opinion of the International Searching Authority dated Oct. 29, 2019, in PCT/US19/44913, citing documents AA-AB, AO-AP and AX therein, 16 pages.
Jackson. A., "Glitter and Face Jewels Festival Makeup Tutorial", Youtube, https://www.youtube.com/watch?v=uhNb41ll7ec, Mar. 9, 2017, times: 4:40-5:00, 8:18-9:45, 3 pages.
Japanese Office Action dated Jun. 6, 2023, in corresponding Japan Patent Application No. 2021-507058 (with Machine translation).

*Primary Examiner* — Danah Al-Awadi
(74) *Attorney, Agent, or Firm* — Oblon, McClelland, Maier & Neustadt, L.L.P.

(57) ABSTRACT

A method for producing a wearable coating having a solid material fixed on skin, the method comprising: A) a step of placing one or more solid materials selected from the group consisting of a powder, a granule, a film, a fiber, a flat material, and a cubic material other than these, on a skin surface; B) a step of, after the step A), electrostatically spraying a composition X comprising the following component (a) and the following component (b) directly on the skin to thereby form a coating on the skin surface: (a) one or more volatile substances selected from the group consisting of water, an alcohol, and a ketone, and (b) a polymer having a coating forming ability; and after the step B) or before the step A), C) a step of applying a composition Y, other than the composition X, comprising one or more components selected from the group consisting of the following component (c) and the following component (d) to the skin: (c) an adhesive polymer, and (d) an oil.

15 Claims, 2 Drawing Sheets

METHOD FOR PRODUCING WEARABLE COATING

TECHNICAL FIELD

The present invention relates to a method for producing a wearable coating.

BACKGROUND ART

Methods of applying wearing articles to skin surfaces by various units are widely carried out. Examples of the methods include a method of applying a paint to a skin surface, a method of mounting a solid material such as beads or jewels on a skin surface, and a method of affixing a printed seal.

As a technique of affixing a printed seal, Patent Literature 1 describes a printable skin-affixing pressure-sensitive adhesive sheet. Further reported is a method of electrostatistically spraying a composition directly on a skin surface having a cosmetic containing a powder applied thereon to form a coating on the skin (Patent Literature 2).

[Patent Literature 1] JP-A-2011-246672
[Patent Literature 2] WO 2017/069080

SUMMARY OF INVENTION

The present invention relates to a method for producing a wearable coating having a solid material fixed on skin, the method comprising:

A) a step of placing one or more solid materials selected from the group consisting of a powder, a granule, a film, a fiber, a flat material, and a cubic material other than these, on a skin surface;

B) a step of, after the step A), electrostatically spraying a composition X comprising the following component (a) and the following component (b) directly on the skin to thereby form a coating on the skin surface:
  (a) one or more volatile substances selected from the group consisting of water, an alcohol, and a ketone, and
  (b) a polymer having a coating forming ability; and after the step B) or before the step A), C) a step of applying a composition Y, other than the composition X, comprising one or more components selected from the group consisting of the following: component (c) and the following component (d) to the skin;
  (c) an adhesive polymer, and
  (d) an oil.

The present invention relates further to a method for producing a wearable coating having a solid material fixed on skin, the method comprising:

A) a step of placing one or more solid materials selected from the group consisting of a powder, a granule, a film, a fiber, and a flat material other than these, on a skin surface;

D) a step of, after the step A), affixing a nanofiber sheet on the skin surface; and after the step D) or before the step A), C) a step of applying a composition Y, other than the composition X, comprising one or more components selected from the group consisting of the following component (c) and the following component (d) to the skin:
  (c) an adhesive polymer, and
  (d) an oil.

The present invention relates further to a method for producing a wearable coating on skin, the method comprising:

B) a step of electrostatically spraying a composition X comprising the following: component (a) and the following component (b) directly on the skin to thereby form a coating on a skin surface;
  (a) one or more volatile substances selected from the group consisting of water, an alcohol, and a ketone, and
  (b) a polymer having a coating forming ability;

C) a step of applying a composition Y, other than the composition X, comprising one or more components selected from the group consisting of the following component (c) and the following component (d) to the skin:
  (c) an adhesive polymer, and
  (d) an oil; and E) a step of, after the step C), applying a wearable article having a color different from a skin color partially to a region having the coating formed thereon to the skin.

DETAILED DESCRIPTION OF INVENTION

Figure 1:
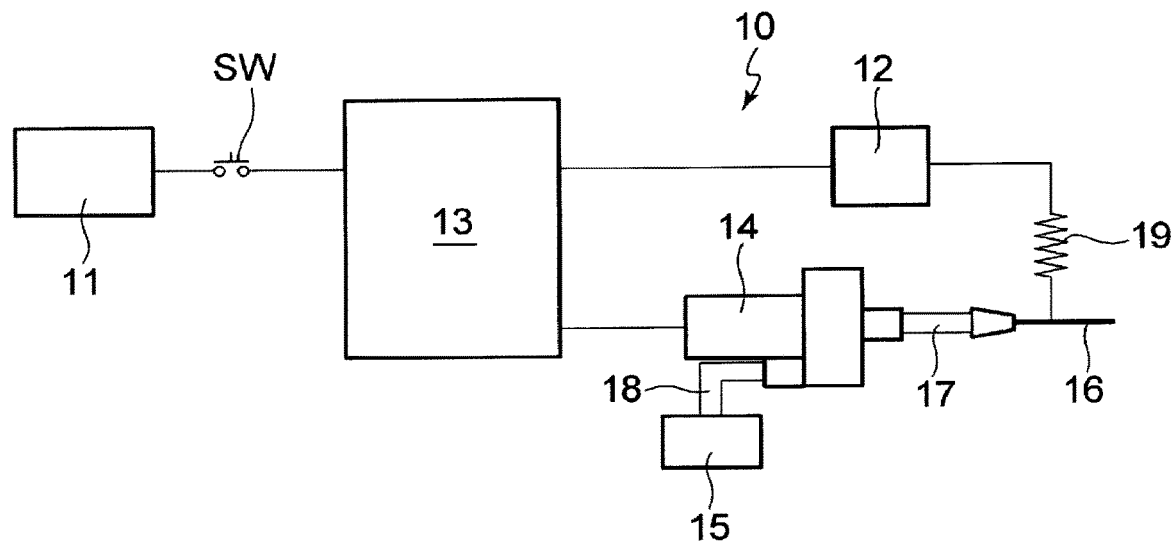
FIG. 1 is a schematic diagram showing an electrostatic spray apparatus suitably used in the present invention.

The above-mentioned printed skin-affixing pressure-sensitive adhesive sheet of Patent Literature 1 causes pressure feeling and uncomfortable feeling to skin and is incompatible with movements of the skin.

Therefore, a unit has been desired for which forms a coating stably fixing wearable articles on skin surfaces, causes no pressure feeling or uncomfortable feeling to skin and has good compatibility with movements of skin.

The present inventors have found that a wearable coating which can stably fix decorations and paints on skin and which causes no pressure feeling or uncomfortable feeling to the skin and is excellent also compatibility with movements of the skin, by combining a step of applying wearable article to a skin surface and electrostatic spraying, with a step of applying a composition containing an adhesive polymer or an oil to the skin surface, to complete the present invention.

The method of the present invention enables the wearable coating to stably fix wearable articles such as decorations, ornamentations, or qualifications and paints composed of solid materials on the skin and causes no pressure feeling or uncomfortable feeling to the skin and has excellent compatibility with movements of skin.

The edge of the formed coating is barely visually recognized and even when the solid materials have protrusions, it is possible to prevent production of gaps between the solid materials and the film obtained by electrostatic spraying. The coating of the film obtained by electrostatic spraying is translucent or transparent and excellent in decorativeness. The film is easy to peel gently, and therefore it is excellent in peelability. Further, the wearable coating, even if sprayed with water or the like, can be prevented from being peeled off, and moreover, the wearable coating can be made one to cause little irritation to skin.

The step A) in the method of the present invention is a step of placing the one or more solid materials selected from the group consisting of a powder, a granule, a film, a fiber, a flat material, and a cubic material other than these, on a skin surface.

The step A) comprises a step, usually carried out, of wearing skin with solid materials. The "wearing skin" in the method of the present invention can include a decorating skin with a solid material, and its purpose may not be limited only to decoration. From the viewpoint of exerting a good appearance, it is preferable to be understood as a decoration. The powder refers to solid materials having 1 μm or more and 1 mm or less in particle width, and specifically includes coloring pigments, coloring powders and bright powders. The coloring pigments include inorganic coloring pigments and organic coloring pigments. The coloring pigments specifically include ones to be used in a step (G) described later. The coloring powders include edible flour, shell powders, bone powders and sands. The bright powders include pearl pigments such as mica, titanium oxide and iron oxide, and metal powders such as aluminum powders and gold powders, and Astroflake, which is a colored metal powder, is also included in the metal powders. Among these, from the viewpoint of decorativeness, adhesiveness, followability, safety and the like on application thereof to skin, preferable is one or more selected from the group consisting of a coloring pigment and a bright powder. Here, the particle width means a diameter when the powder is spherical, and it means a maximum width when the particle is not spherical; alternatively the particle width means a diameter measured by a laser diffraction scattering method.

The granule refers to solid materials of 1 mm or more and 5 mm or less in particle width, and specifically includes metal particles, resin particles, stones and shells. Examples of the resin particles include beads and resin particles whose outer surfaces are colored. The stones include rhinestones and jewels. Among these, from the viewpoint of decorativeness, adhesiveness, followability, safety and the like on application thereof to skin, preferable is one or more selected from the group consisting of a metal particle, a resin particle and a stone.

Here, the particle width means a diameter when the granule is spherical, and the particle width means a maximum width when the particle is not spherical; alternatively the particle width means a size measured by a sieve method.

The film is a solid material other than the above-mentioned powder and granule, and includes paper, metal foils and resin films and colored or metal-deposited films thereof, and these films having granules adhered thereon. The paper includes Japanese paper and kraft paper; the metal foils include gold foils, silver foils and other metal foils; and the resin films include films such as nylon films and polyethylene films; and the colored or metal-deposited films include hologram films. Among these, from the viewpoint of decorativeness, adhesiveness, followability, safety and the like on application thereof to skin, preferable are the paper, the metal foils and the resin films.

The fiber includes plant fibers such as cotton and hemp ones, animal fibers such as silk and wool ones, regenerated fibers such as rayon and cupra ones, semisynthetic fibers such as acetate ones, and synthetic fibers such as nylon and polyester ones; and mixtures thereof are included.

The flat material is a flat material other than the above-mentioned powder and granule, and includes flat materials having, for example, a thickness of preferably 0.1 mm or more and more preferably 0.5 mm or more, and preferably 5 mm or less and more preferably 2 mm or less, and a maximum width of more than 5 mm. Examples of the flat material include metal plates, plastic plates, rubber plates, cloths such as fabrics and nonwoven fabrics, and natural materials such as pressed flowers, plants, shells and eggshells.

The cubic material other than the powder, granule, fiber and flat material includes solid materials having more than 5 mm in both width and height, and additionally solid materials having gaps or irregularities, such as accordion shapes and flowers.

The solid material such as powder, granule, fiber and flat material include microchip, electronic circuit, bar code, GR code and the like. The microchip, electronic circuit, bar code and GR code and the like may include those having a function of a key for locking/unlocking, an admission ticket, a traffic ticket, a sensor, a measuring instrument, a transmitter, GPS (global positioning system), a communication device, a lighting, an imaging device, and the like.

In the step A), one or more of these solid materials can be used. Examples of the usable materials include combinations of the powder with the granule. It is preferable that the step A) place each of a plurality of solid materials discontinuously on a skin surface. Specifically, preferable is, not usual application of foundations, but formation of patterns made discontinuous; and the foundations are excluded from materials to be placed in the step A). It is preferable that no continuous solvent be present between the solid materials in the step A). A method for placing the solid materials on a skin surface is preferably a method, not accompanied by friction, including scattering, mounting, spraying and using an air brush. The solid materials in the step A) preferably have colors different from a color of a skin for the solid materials to be applied to, and may contain transparent or translucent solid materials. Being a color different from a skin color refers to that the color difference E, represented by the following expression, between the skin and the wearable articles is 3 or more and more preferably 5 or more:

$$\Delta E = (\Delta a^2 + \Delta b^2 + \Delta L^2)^{1/2} \quad \text{(Expression 1)}$$

where a, b and L are based on the CIE colorimetric system.

The step B) is a step of electrostatically spraying the composition X comprising a component (a) and a component (b) directly on skin to thereby form a coating on the skin surface.

As a method for forming the coating in the step B), the present invention adopts an electrostatic spray method. The electrostatic spray method is a method in which a positive or negative high voltage is applied to a composition to charge the composition, and the charged composition is sprayed or discharged toward a target. The sprayed composition, while repeating micronization by the Coulomb repulsive force, spreads in a space, and in the course, or after the sprayed composition is adhered on the target, a solvent serving as a volatile substance dries to thereby form the coating on a surface of the target.

The above-mentioned composition X (hereinafter, referred to also as "spraying composition") to be used in the present invention is a liquid in an environment where the electrostatic spray method is carried out. The composition X comprises the following component (a) and component (b).

Component (a) One or more volatile substances selected from the group consisting of water, an alcohol, and a ketone.

Component (b) A polymer having a coating forming ability.

Hereinafter, the each component will be described.

The volatile substance of the component (a) is a substance having volatility in its liquid state. The component (a) is blended in the spraying composition for the purpose that the spraying composition placed in an electric field, after fully charged, is discharged toward a skin from a nozzle tip, and the charge density of the spraying composition becomes excessive as the component (a) evaporates, and the component (a) further evaporates while the component (a) is further micronized by the Coulomb repulsion to thereby finally form a dry coating on the skin. For this purpose, the vapor pressure at 20° C. of the volatile substance is preferably 0.01 kPa or more and 106.66 kPa or less, more preferably 0.13 kPa or more and 66.66 kPa or less, even more preferably 0.67 kPa or more and 40.00 kPa or less and further more preferably 1.33 kPa or more and 40.00 kPa or less.

Among the volatile substances of the component (a), as an alcohol, for example, a monohydric chain aliphatic alcohol, a monohydric alicyclic alcohol or a monohydric aromatic alcohol is preferably used. The monohydric aliphatic alcohol includes $C_1$ to $C_6$ alcohols; the monohydric alicyclic alcohol includes $C_4$ to $C_6$ cyclic alcohols; and the monohydric aromatic alcohol includes benzyl alcohol and phenylethyl alcohol. Specific examples thereof include ethanol, isopropyl alcohol, butyl alcohol, phenylethyl alcohol, n-propanol and n-pentanol. As the alcohol, one or two or more selected from these alcohols can be used.

Among the volatile substances of the component (a), the ketone includes di-$C_1$-$C_4$ alkyl ketones such as acetone, methyl ethyl ketone and methyl isobutyl ketone. These ketones can be used singly or in a combination of two or more.

The volatile substance of the component (a) is preferably one or more selected from the group consisting of ethanol, isopropyl alcohol, butyl alcohol and water, more preferably one or more selected from the group consisting of ethanol and butyl alcohol, and even more preferably a volatile substance containing at least ethanol.

The content of the component (a) in the spraying composition is preferably 30% by mass or more, more preferably 55% by mass or more and even more preferably 60% by mass or more. Then the content is preferably 98% by mass or less, more preferably 96% by mass or less and even more preferably 94% by mass or less. The content of the component (a) in the spraying composition is preferably 30% by mass or more and 98% by mass or less, more preferably 55% by mass or more and 96% by mass or less and even more preferably 60% by mass or more and 94% by mass or less. Incorporation of the component (a) in this proportion in the spraying composition enables the spraying composition to be sufficiently volatilized when the electrostatic spray method is carried out.

Ethanol is, with respect to the total amount of the volatile substances of the component (a), preferably 50% by mass or more, more preferably 65% by mass or more and even more preferably 80% by mass or more. Being 100% by mass or less is preferable. Ethanol is, with respect to the total amount of the volatile substances of the component (a), preferably 50% by mass or more and 100% by mass or less, more preferably 65% by mass or more and 100% by mass or less and even more preferably 80% by mass or more and 100% by mass or less.

Further, water is, from the viewpoint of fiber formability and electroconduction, with respect to the total amount of the volatile substances of the component (a), preferably less than 50% by mass, more preferably 45% by mass or less, even more preferably 10% by mass or less and further more preferably 5% by mass or less, and preferably 0.2% by mass or more and more preferably 0.4% by mass or more.

The polymer having the coating forming ability as the component (b) is usually a substance which can be dissolved in the volatile substance as the component (a). Here, being dissolved refers to being in a dispersed state at 20° C., which dispersed state is a visually homogeneous state, preferably a visually transparent or translucent state.

As the polymer having the coating forming ability, a suitable one is used according to the property of the volatile substance of the component (a). Specifically, the polymers having the coating forming ability are roughly classified into water-soluble polymers and water-insoluble polymers. In the present description, the "water-soluble polymer" refers to a polymer having such a property that 1 g of the polymer is weighed in the environment of 1 atm and 23° C., and thereafter dipped in 10 g of ion-exchange water, and after an elapse of 24 hours, 0.5 g or more of the dipped polymer dissolves in the water. Meanwhile, in the present description, the "water-insoluble polymer" refers to a polymer having such a property that 1 g of the polymer is weighed in the environment of 1 atm and 23° C., and thereafter dipped in 10 g of ion-exchange water, and after an elapse of 24 hours, 0.5 g or more of the dipped polymer does not dissolve in the water.

Examples of the water-soluble polymer having the coating forming ability include mucopolysaccharides such as pullulan, hyaluronic acid, chondroitin sulfuric acid, poly-γ-glutamic acid, denatured cornstarch, β-glucan, glucooligosaccharides, heparin and keratosulfuric acid, natural polymers such as cellulose, pectin, xylan, lignin, glucomannan, galacturonic acid, psyllium seed gum, tamarind seed gum, gum arabic, tragacanth gum, soybean water-soluble polysaccharides, alginic acid, carrageenan, laminaran, agar (agarose), fucoidan, methylcellulose, hydroxypropylcellulose and hydroxypropylmethylcellulose, and synthetic polymers such as partially saponified polyvinyl alcohols (if not used concurrently with a crosslinking agent), low-saponified polyvinyl alcohols, polyvinyl pyrrolidone (PVP), polyethylene oxide, sodium polyacrylate, water-soluble polyester resins and water-soluble nylon. These water-soluble polymers can be used singly or in a combination of two or more. Among these water-soluble polymers, from the viewpoint of ease of production of coatings, it is preferable to use pullulan, and synthetic polymers such as partially saponified polyvinyl alcohols, low-saponified polyvinyl alcohols, polyvinyl pyrrolidone and polyethylene oxide. In using a polyethylene oxide as the water-soluble polymer, the number-average molecular weight thereof is preferably 50,000 or more and 3,000,000 or less and more preferably 100,000 or more and 2,500,000 or less.

Meanwhile, examples of the water-insoluble polymer having the coating forming ability include completely saponified polyvinyl alcohols can be insolubilized after formation of coatings, partially saponified polyvinyl alcohols can be crosslinked after formation of coatings by concurrent use of a crosslinking agent, oxazoline-modified silicones of poly(N-propanoylethyleneimine)-graft-dimethylsiloxane/γ-aminopropylmethylsiloxane copolymers or the like, polyvinylacetal diethylaminoacetate, zein (major component of corn protein), polyester, polylactic acid (PLA), acryl resins such as polyacrylonitrile resins and polymethacrylate resins, polystyrene resins, polyvinylbutyral resins, polyethylene terephthalate resins, polybutylene terephthalate resins, polyurethane resins, polyamide resins, polyimide resins and polyamideimide resins. These water-insoluble polymers can be used singly or in a combination of two or more. Among these water-insoluble polymers, it is preferable to use one or more selected from the group consisting of completely saponified polyvinyl alcohols can be being insolubilized after formation of coatings, partially saponified polyvinyl alcohols can be crosslinked after formation of coatings by concurrent use of a crosslinking agent, polyvinylbutyral resins, polyurethane resins, oxazoline-modified silicones of poly(N-propanoylethyleneimine)-graft-dimethylsiloxane/γ-aminopropylmethylsiloxane copolymers or the like, polyvinylacetal diethylaminoacetate and zein; and it is more preferable to use one or more selected from the group consisting of polybutyral resins and polyurethane resins.

The content of the component (b) in the spraying composition is preferably 2% by mass or more, more preferably 4% by mass or more and even more preferably 6% by mass or more. The content is preferably 50% by mass or less, more preferably 45% by mass or less and even more preferably 40% by mass or less. The content of the component (b) in the spraying composition is preferably 2% by mass or more and 50% by mass or less, more preferably 4% by mass or more and 45% by mass or less and even more preferably 6% by mass or more and 40% by mass or less. Containing the component (b) in this proportion in the spraying composition successfully enables to form a coating composed of a deposit of fibers, which masks the surface of bare skin, is excellent in scratch resistance and extensibility, and is excellent in cosmetic persistency.

The ratio of the contents of the component (a) and the component (b), ((a)/(b)), in the spraying composition is, from the viewpoint that the component (a) can be sufficiently volatilized when the electrostatic spray method is carried out, preferably 0.5 or more and 40 or less, more preferably 1 or more and 30 or less and even more preferably 1.3 or more and 25 or less.

The ratio of ethanol and the content of the component (b), (ethanol/(b)), in the spraying composition is, from the viewpoint that ethanol can be sufficiently volatilized when the electrostatic spray method is carried out, preferably 0.5 or more and 40 or less, more preferably 1 or more and 30 or less and even more preferably 1.3 or more and 25 or less.

The spraying composition can comprise a glycol. The glycol includes ethylene glycol, propylene glycol, butylene glycol, diethylene glycol and dipropylene glycol. From the viewpoint that the component (a) can be sufficiently volatilized when the electrostatic spray method is carried out, the glycol is, in the spraying composition, preferably 10% by mass or less and more preferably 8% by mass or less.

The spraying composition can further contain a powder. The powder includes coloring pigments, extender pigments, pearl pigments and organic powders. The powder is, from the viewpoint of imparting smooth feel to skin surfaces, in the spraying composition, preferably 5% by mass or less, more preferably 3% by mass or less and even more preferably 1% by mass or less, and it is preferable to contain substantially no powder.

The spraying composition may contain only the above-mentioned component (a) and component (b), or may contain, in addition to the component (a) and component (b), other components. Examples of the other components include oils such as di(phytosteryl/octyldodecyl) lauroylglutamate, surfactants, UV protective agents, fragrances, repellants, antioxidants, stabilizers, antiseptics, antiperspirants and various vitamins. Here, these agents are not limited to their original applications as the agents, but can be used for other applications according to purposes, for example, an antiperspirant can be used as a fragrance. Alternatively, these agents can be used as having multiple purposes; for example, an antiperspirant can also serve as a fragrance. Where the spraying composition contains the other components, the content rate of the other components is preferably 0.1% by mass or more and 30% by mass or less and more preferably 0.5% by mass or more and 20% by mass or less.

In the method of the present invention, before or after the step B, a coating is formed directly on a skin surface by electrostatically spraying the spraying composition.

When the electrostatic spray method is carried out, preferably used is a spraying composition whose viscosity at 25° C. is 1 mPa·s or more, more preferably 10 mPa·s or more and even more preferably 50 mPa·s or more. Also preferably used is a spraying composition whose viscosity at 25° C. is 5,000 mPa·s or less, more preferably 2,000 mPa·s or less and even more preferably 1,500 mPa·s or less. The viscosity at 25° C. of the spraying composition is preferably 1 mPa·s or more and 5,000 mPa·s or less, more preferably 10 mPa·s or more and 2,000 mPa·s or less and even more preferably 50 mPa·s or more and 1,500 mPa·s or less. Use of the spraying composition having a viscosity in this range successfully enables formation of a coating, particularly a porous coating composed of a deposit of fibers, by the electrostatic spray method. The formation of the porous coating is advantageous from the viewpoint of improving prevention of stuffiness of skin, from the viewpoint of improving adhesiveness of the coating to skin, from the viewpoint that the coating, when peeled off the skin, can be peeled off easily and cleanly, and from other viewpoints. The viscosity of the spraying composition is measured at 25° C. by using an E-type viscometer. As the E-type viscometer, for example, an E-type viscometer, manufactured by Tokyo Keiki Inc. can be used. As a rotor in this case, a rotor No. 43 can be used.

The spraying composition is sprayed directly on a skin of a human by the electrostatic spray method. The electrostatic spray method comprises, in an electrostatic spraying step, a step of electrostatically spraying the spraying composition on a skin by using an electrostatic spray apparatus to thereby form a coating. The electrostatic spray apparatus has a container accommodating the spraying composition, a nozzle for discharging the spraying composition, a supply device for supplying the spraying composition accommodated in the container to the nozzle, and a power source for applying a voltage to the nozzle. FIG. 1 shows a schematic diagram indicating an electrostatic spray apparatus suitably used in the present invention. An electrostatic spray apparatus 10 shown in FIG. 1 has a low-voltage power source 11. The low-voltage power source 11 is one which can generate a voltage of several volts to several tens of volts. For the purpose of enhancing transportability of the electrostatic spray apparatus 10, it is preferable that the low-voltage power source 11 be composed of one or more batteries. Use of batteries as the low-voltage power source 11 exhibits also such an advantage that the batteries can be exchanged easily as required. In place of the batteries, an AC adaptor or the like can be used as the low-voltage power source 11.

The electrostatic spray apparatus 10 has also a high-voltage power source 12. The high-voltage power source 12 is connected to the low-voltage power source 11, and has an electronic circuit (not shown in figure) for boosting a voltage generated by the low-voltage power source 11 to a high voltage. The boosting electronic circuit is usually constituted of a transformer, capacitors, semiconductor elements and the like.

The electrostatic spray apparatus 10 further has an auxiliary electric circuit 13. The auxiliary electric circuit 13 intervenes between the above-mentioned low-voltage power source 11 and high-voltage power source 12, and has a function of regulating the voltage of the low-voltage power source 11 to cause the high-voltage power source 12 to stably operate. The auxiliary electric circuit 13 further has a function of controlling the rotation frequency of a motor equipped with a pump mechanism 14 described later. The control of the rotation frequency of the motor leads to control of the amount of the spraying composition supplied from a container 15 described later of the spraying composition to the pump mechanism 14. A switch SW is installed between the auxiliary electric circuit 13 and the low-voltage power source 11, and is so configured that the electrostatic spray apparatus 10 can be operated/stopped by on/off of the switch SW.

The electrostatic spray apparatus 10 further has a nozzle 16. The nozzle 16 is composed of various electroconductors including metals and non-electroconductors such as plastics, rubbers and ceramics, and has a shape which can discharge the spraying composition from its tip. In the nozzle 16, a fine space through which the spraying composition flows is formed along the longitudinal direction of the nozzle 16. It is preferable that the size of the fine space be 100 µm or more and 1,000 µm or less in diameter. The nozzle 16 communicates with the pump mechanism 14 through a pipe 17. The pipe 17 may be an electroconductor or a non-electroconductor. Then, the nozzle 16 is electrically connected to the high-voltage power source 12. Thereby, the nozzle 16 is so configured that a high voltage can be applied thereto. In this case, in order to prevent an excessive current from flowing in a human body when the human body touches directly the nozzle 16, the nozzle 16 and the high-voltage power source 12 are electrically connected through a current limiting resistance 19.

The pump mechanism 14 communicating with the nozzle 16 through the pipe 17 functions as a supply device for supplying the spraying composition accommodated in the container 15 to the nozzle 16. The pump mechanism 14 operates by receiving a power from the low-voltage power source 11. The pump mechanism 14 is constituted so as to supply a predetermined amount of the spraying composition to the nozzle 16 under control by the auxiliary electric circuit 13.

To the pump mechanism 14, the container 15 is connected through a flexible pipe 18. The spraying composition is accommodated in the container 15. It is preferable that the container 15 have a cartridge-type exchangeable form. It is preferable that the pump mechanism 14 be of a gear pump type or a piston pump type.

Figure 2:
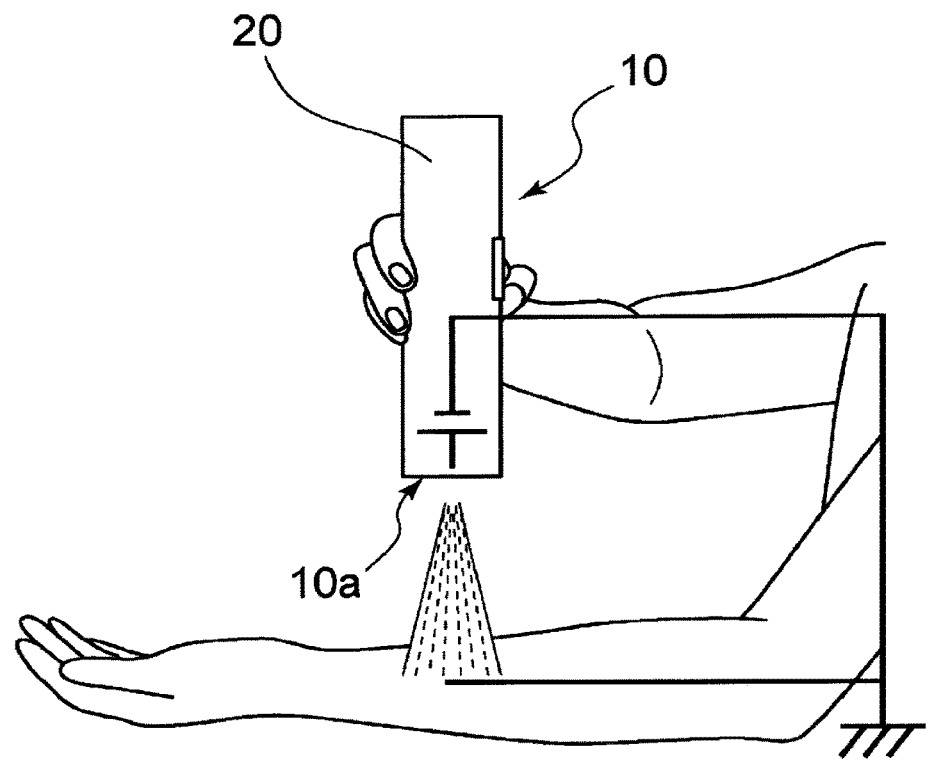
FIG. 2 is an illustrative view showing the state of carrying out an electrostatic spray method using an electrostatic spray apparatus.

The electrostatic spray apparatus 10 having the above constitution can be used, for example, as shown in FIG. 2. FIG. 2 shows a hand-held type electrostatic spray apparatus 10 having a size holdable by one hand. The electrostatic spray apparatus 10 shown in the figure is so configured that all members of the schematic diagram shown in FIG. 1 are accommodated in a cylindrical housing 20. On one end 10a in the longitudinal direction of the housing 20, a nozzle (not shown in figure) is disposed. The nozzle is arranged on the housing 20 so as to protrude toward a skin side as a coating forming target so that the jetting direction of the composition is made to coincide with the longitudinal direction of the housing 20. By arranging the nozzle so that the nozzle tip protrudes toward a coating forming target in the longitudinal direction of the housing 20, it becomes hard for the spraying composition to adhere on the housing and a coating can be formed stably.

Where a skin as the coating forming target is a user's own skin, when an electrostatic spray apparatus 10 is operated, the user, that is, a person forming a coating on the person's own skin by electrostatic spraying, holds the apparatus 10 by hand and directs one end 10a of the apparatus 10 having a nozzle (not shown in figure) arranged thereon toward a target site of electrostatic spraying. FIG. 2 illustrates a state that the one end 10a of the electrostatic spray apparatus 10 is directed to an inner side of the user's forearm. Under this state, a switch of the apparatus 10 is turned on to carry out the electrostatic spray method. A power is supplied to the apparatus 10 to generate an electric field between the nozzle and the skin. In an embodiment illustrated in FIG. 2, a high positive voltage is applied to the nozzle and the skin becomes a negative electrode. When the electric field is generated between the nozzle and the skin, the spraying composition on the nozzle tip is depolarized by electrostatic induction and the frontend portion of the spraying composition spreads to a cone-like shape; and charged droplets of the spraying composition are discharged from the spread cone frontend along the electric field into the air toward the skin. As the component (a) serving as a solvent evaporates from the charged spraying composition discharged into the space and, the charge density of the surface of the spraying composition becomes excessive, so that while micronization of the spraying composition is repeated by the Coulomb repellency, the spraying composition spreads into the space and reaches the skin. In this case, by suitably regulating the viscosity of the spraying composition, the sprayed spraying composition can be made to reach the skin in the state of being droplets. Alternatively, it is also possible that during the discharge into the space, the component (a) of a volatile substance serving as a solvent is caused to volatilize from the composition to cause a polymer serving as a solute having the coating forming ability to solidify, the spraying composition is caused to extensionally deform due to a potential difference and form fibers, which deposit on the surface of the skin. For example, when the viscosity of the spraying composition is raised, it becomes easy for the composition to be deposited in a form of fibers on the skin surface. Thereby, a coating composed of a deposit of the fibers is formed on the skin surface. A coating composed of a deposit of fibers is possible to form also by regulating the distance between the nozzle and the skin, and the voltage applied to the nozzle.

During carrying out of the electrostatic spray method, a high potential difference is generated between the skin which is a coating forming target and the nozzle. Since the impedance is very high, however, the current flowing in the human body is remarkably minute. The present inventors have confirmed that the current flowing in a human body during carrying out of the electrostatic spray method is lower by several digits than, for example, the current flowing in human bodies due to a static electricity generated in usual lives.

In forming a deposit of fibers by the electrostatic spray method, the thickness of the fibers is, in terms of equivalent circle diameter, preferably 10 nm or more and more preferably 50 nm or more. Then, the thickness is preferably 3,000 nm or less and more preferably 2,000 nm or less. The thickness of the fibers can be measured, for example, by observing the fibers in a magnification of 10,000× by a scanning electron microscope (SEM) observation, arbitrarily choosing 10 fibers excluding defects (lumps of fibers, crossing portions of fibers, droplets) from its two-dimensional image, drawing lines orthogonal to the longitudinal directions of the fibers, and directly reading the fiber diameters.

The above fiber, under the principle of its production, becomes an infinite-length continuous fiber, but it is preferable that the fiber have a length at least 100 or more times a thickness of the fiber. In the present description, a fiber having a length 100 or more times a thickness of the fiber is defined as a "continuous fiber". Then, it is preferable that a coating produced by the electrostatic spray method be a porous discontinuous coating composed of a deposit of continuous fibers. The coating of such a form not only can be handled as one sheet as an aggregate, but also has a feature of being very soft, and has advantages of not falling into pieces even under a shearing force and excellence in followability to movements of the body. The coating also has an advantage of excellence in diffusibility of sweat generated from skin. The coating further also has an advantage of being easily peeled off. By contrast, a continuous coating having no pores is not easily peeled off and since the diffusibility of sweat is very low, easily causes stuffiness on skin.

The spraying composition having become fibrous reaches a skin, in a charged state. Since the skin is also charged as described before, the fibers adhere closely with the skin by an electrostatic force. Since fine irregularities such as texture are present on the surface of skin, the fibers adhere more closely with the skin surface conjointly with the anchor effect by the irregularities. When the electrostatic spraying is thus completed, the power source of the electrostatic spray apparatus 10 is turned off. Thereby, the electric field between the nozzle and the skin vanishes and charges are immobilized on the skin surface. Consequently, the adhesiveness of the coating further develops.

Although the above description has been for a porous coating composed of a deposit of fibers as the coating, forms of coatings are not limited thereto; a continuous coating having no pores may be formed; or a porous coating having a form other than a deposit of fibers, for example, a porous coating made by irregularly or regularly forming a plurality of throughholes on a continuous coating, that is, a discontinuous coating may be formed. As described above, by controlling the viscosity of the spraying composition, the distance between the nozzle and a skin, the voltage applied to the nozzle, and the like, a coating having an optional shape can be formed.

It is preferable, for successfully forming a coating, that the distance between the nozzle and a skin is, though depending also on the voltage applied to the nozzle, 50 mm or more and 150 mm or less. The distance between the nozzle and a skin can be measured by a noncontact type sensor usually used, or the like.

Irrespective of whether or not a coating formed by the electrostatic spray method is porous, the basis weight of the coating is preferably 0.1 $g/m^2$ or more and more preferably 1 $g/m^2$ or more. Then, the basis weight is preferably 30 $g/m^2$ or less and more preferably 20 $g/m^2$ or less. The basis weight of the coating is, for example, preferably 0.1 $g/m^2$ or more and 30 $g/m^2$ or less and more preferably 1 $g/m^2$ or more and 20 $g/m^2$ or less. By thus setting the basis weight of a coating, the adhesiveness of the coating can be improved. Then, the electrostatic spray step of electrostatically spraying the composition directly on a skin to thereby form a coating means a step of carrying out electrostatic spraying on a skin to thereby form a coating. A step of electrostatically spraying a composition on a place other than a skin to form a sheet composed of fibers, and applying the sheet to a skin surface is different from the above electrostatic spray step.

Then, the step C) will be described.

The step C) is a step of applying, to the skin, the composition Y, other than the composition X (spraying composition), comprising one or more selected from the group consisting of a component (c) and a component (d). The step C) is carried out after the electrostatic spray step B) or before the step A).

(c) An adhesive polymer
(d) An oil

The step C) is a step of applying the composition Y to a skin surface by using a unit other than electrostatic spraying.

The (c) adhesive polymer to be used for the composition Y contributes to the stable fixation on the skin of the solid materials by the coating formed on the skin by electrostatic spraying, and the improvement of followability of the coating to movements of the skin. As the adhesive polymer, one which is usually used as an adhesive agent or a pressure-sensitive adhesive agent can be used. Examples thereof include rubber-based adhesive polymers, silicone-based adhesive polymers, acrylic adhesive polymers and urethane-based adhesive polymers, and one or more selected therefrom can be used. As the (c) adhesive polymer, at least one selected from the group consisting of a nonionic polymer, an anionic polymer, a cationic polymer and an amphoteric polymer can be used. It is preferable that the (c) adhesive polymer be a polymer other than a polymer of the component (b).

Examples of the rubber-based adhesive polymers include ones produced by using, as a base polymer, a natural rubber; a synthetic rubber such as polyisoprene rubber, styrene-butadiene (SB) rubber, styrene-isoprene (SI) rubber, styrene-isoprene-styrene block copolymer (SIS) rubber, styrene-butadiene-styrene block copolymer (SBS) rubber, styrene-ethylene-butylene-styrene block copolymer (SEBS) rubber, styrene-ethylene-propylene-styrene block copolymer (SEPS) rubber, styrene-ethylene-propylene block copolymer (SEP) rubber, reclaimed rubber, butyl rubber, polyisobutylene or a modified substance of these; or the like.

Among these rubber-based adhesive polymers, more preferable is at least one selected from the group consisting of a styrene-isoprene-styrene block copolymer, a styrene-butadiene-styrene block copolymer, a styrene-butadiene rubber, a polyisobutylene, a polyisoprene rubber and a silicone rubber. A commercially available product of the rubber-based adhesive polymer includes Yodosol GH41F (manufactured by Akzo Nobel N.V.).

Examples of the acrylic adhesive polymers include ones produced by using, as a base polymer, an acrylic polymer (homopolymer or copolymer) produced by using, as a monomer component, one or more alkyl (meth)acrylates. Specific examples of the alkyl (meth)acrylates include C1-20 alkyl (meth)acrylates such as methyl (meth)acrylate, ethyl (meth)acrylate, propyl (meth)acrylate, isopropyl (meth)acrylate, butyl (meth)acrylate, isobutyl (meth)acrylate, s-butyl (meth)acrylate, t-butyl (meth)acrylate, pentyl (meth)acrylate, hexyl (meth)acrylate, heptyl (meth)acrylate, octyl (meth)acrylate, 2-ethylhexyl (meth)acrylate, isooctyl (meth)acrylate, nonyl (meth)acrylate, isononyl (meth)acrylate, decyl (meth)acrylate, isodecyl (meth)acrylate, undecyl (meth)acrylate, dodecyl (meth)acrylate, tridecyl (meth)acrylate, tetradecyl (meth)acrylate, pentadecyl (meth)acrylate, hexadecyl (meth)acrylate, heptadecyl (meth)acrylate, octadecyl (meth)acrylate, nonadecyl (meth)acrylate and eicosyl methacrylate.

Auxiliary monomers to be used together with these base polymers include N-vinylpyrrolidone, methylvinylpyrrolidone, (meth)acrylic acid and vinyl acetate. Commercially available products of the acrylic polymers include Amphomer 28-4910 (manufactured by Akzo Nobel N.V.), Yodosol GH256F (manufactured by Akzo Nobel N.V., particle diameter: 20 to 40 nm), Yodosol GH800F (manufactured by Akzo Nobel N.V.), Yodosol GH810F (manufactured by Akzo Nobel N.V.), Daitosol 5000AD (manufactured by Daito Kasei Kogyo Co., Ltd.) and Daitosol 5000SJ (manufactured by Daito Kasei Kogyo Co., Ltd.).

As the silicone-based adhesive polymer, there is preferably used, for example, a silicone-based adhesive polymer produced by using, as a base polymer, a silicone rubber or silicone resin containing organopolysiloxane. As the base polymer constituting the silicone-based adhesive polymer, there may be used a base polymer produced by crosslinking the silicone rubber or silicone resin. Examples of the silicone rubber include organopolysiloxanes containing dimethylsiloxane as their constituting unit. To the organopolysiloxanes, as required, a functional group (for example, a vinyl group) may be introduced. Examples of the silicone resin include organopolysiloxanes containing, as their constituting unit, at least one constituting unit selected from the group consisting of an $R_3SiO_{1/2}$ constituting unit, a $SiO_2$ constituting unit, an $RSiO_{3/2}$ constituting unit and an $R_2SiO$ constituting unit. The silicone-based adhesive polymer may contain a crosslinking agent. Examples of the crosslinking agent include siloxane-based crosslinking agents and peroxide-based crosslinking agents. As the peroxide-based crosslinking agent, an optional suitable one can be used. Examples of the peroxide-based crosslinking agent include benzoyl peroxide, t-butyl peroxybenzoate and dicumyl peroxide. Examples of the siloxane-based crosslinking agent include polyorganohydrogensiloxane.

As the organopolysiloxane, the following poly(N-acylalkyleneimine)-modified organopolysiloxane (hereinafter, referred to also simply as "modified organopolysiloxane") can be used.

The modified organopolysiloxane is one made by binding a poly(N-acylalkyleneimine) segment composed of a repeating unit represented by the following general formula (1):

(1)

in the formula, $R^1$ denotes a hydrogen atom, an alkyl group having 1 to 22 carbon atoms, an aralkyl group or an aryl group, to at least two silicon atoms of an organopolysiloxane segment constituting its main chain, through an alkylene group containing a heteroatom, wherein in the modified organopolysiloxane, the mass ratio of the organopolysiloxane segment (α) constituting its main chain and the poly(N-acylalkyleneimine) segment (β), (α/β), is 40/60 or more and 98/2 or less; and the weight-average molecular weight of the organopolysiloxane segment constituting its main chain is 30,000 or more and 100,000 or less.

The mass ratio of the organopolysiloxane segment (α) and the poly(N-acylalkyleneimine) segment (β), (α/β), in the modified organopolysiloxane is, from the viewpoint of improving friction resistance of a coating, preferably 40/60 or more, more preferably 55/45 or more and even more preferably 65/35 or more. Further, the ratio is, from the viewpoint of forming a coating in a fibrous form, preferably 98/2 or less, more preferably 90/10 or less and even more preferably 82/18 or less.

In the modified organopolysiloxane, although at least two poly(N-acylalkyleneimine) segments can be bound to any silicon atoms constituting the organopolysiloxane segment through an alkylene group containing a heteroatom, it is preferable that the poly(N-acylalkyleneimine) segment be bound to one or more silicon atoms excluding ones on both the terminals through the above alkylene group, and it is more preferable that the poly(N-acylalkyleneimine) segments be bound to two or more silicon atoms excluding ones on both the terminals through the above alkylene group.

The alkylene group containing a heteroatom intervening in the binding of the organopolysiloxane segment and the poly(N-acylalkyleneimine) includes alkylene groups having 2 to 20 carbon atoms containing 1 to 3 nitrogen atoms, oxygen atoms and/or sulfur atoms. Specific examples thereof include the following.

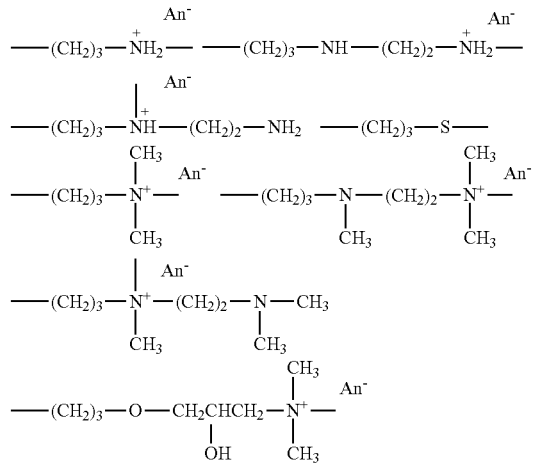

[in the formulae, An⁻ denotes an anion.]

An N-acylalkyleneimine unit constituting the poly(N-acylalkyleneimine) segment is represented by the above general formula (1); in the general formula (1), examples of the alkyl group having 1 to 22 carbon atoms of $R^1$ include straight-chain, branched or cyclic alkyl groups having 1 to 22 carbon atoms; and specific examples thereof include a methyl group, an ethyl group, an n-propyl group, an isopropyl group, an n-butyl group, a tert-butyl group, a pentyl group, a hexyl group, a cyclohexyl group, a heptyl group, an octyl group, a nonyl group, a decyl group, an undecyl group, a dodecyl group, an octadecyl group, a nonadecyl group, an eicosyl group and a docosyl group.

Examples of the aralkyl group include aralkyl groups having 7 to 15 carbon atoms, and specific examples thereof include a benzyl group, a phenethyl group, a trityl group, a naphthylmethyl group and an anthracenylmethyl group.

Examples of the aryl group include aryl groups having 6 to 14 carbon atoms, and specific examples thereof include a phenyl group, a tolyl group, a xylyl group, a naphthyl group, a biphenyl group, an anthryl group and a phenanthryl group.

Here, in the present description, the mass ratio (α/β) refers to a value obtained by dissolving a modified organopolysiloxane in 5% by mass in heavy chloroform, subjecting the solution to a nuclear magnetic resonance ($^1$H-NMR) analysis, and determining an integral ratio of an alkyl group or a phenyl group in organopolysiloxane segments to a methylene group in poly(N-acylalkyleneimine) segments.

Then, in the modified organopolysiloxane, the weight-average molecular weight (MWg) of an organopolysiloxane segment between neighboring poly(N-acylalkyleneimine) segments is preferably 1,300 or more, more preferably 1,500 or more and even more preferably 1,800 or more, and preferably 32,000 or less, more preferably 10,000 or less and even more preferably 5,000 or less.

In the present description, the "organopolysiloxane segment between neighboring poly(N-acylalkyleneimine) segments" is, as represented in the following formula (2), a moiety encircled by dashed lines between two points from a binding point (binding point A) of an organopolysiloxane segment with a poly(N-acylalkyleneimine) segment to a binding point (binding point B) of the organopolysiloxane segment with a neighboring poly(N-acylalkyleneimine) segment, and refers to a segment constituted of one $R^2SiO$ unit, one $R^6$ and (y+1) $R^2{}_2SiO$ units. Further, the "poly(N-acylalkyleneimine) segment" refers to —Z—$R^7$ bound to the above $R^6$.

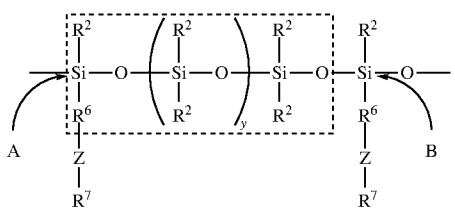

(2)

In the general formula (2), $R^2$ each independently denote an alkyl group having 1 to 22 carbon atoms or a phenyl group; $R^6$ denotes an alkylene group containing a heteroatom; $R^7$ denotes a residue of a polymerization initiator; —Z—$R^7$ denotes a poly(N-acylalkyleneimine) segment; and y denotes a positive number.

The MWg, though being a molecular weight of the moiety encircled by dashed lines in the above general formula (2), can be interpreted as a mass (g/mol) of organopolysiloxane segments per 1 mol of poly(N-acylalkyleneimine) segments, and when 100% of functional groups of an organopolysiloxane serving as a raw material compound is substituted by the poly(N-acylalkyleneimine), coincides with the functional group equivalent weight (g/mol) of a modified organopolysiloxane.

Where the functional group equivalent weight (g/mol) of the organopolysiloxane serving as a raw material compound has already been known, the MWg, even where 100% of the functional groups is not substituted by the poly(N-acylalkyleneimine), can be calculated by the following expression.

MWg=[a functional group equivalent weight (g/mol) of an organopolysiloxane]/[a substitution rate (%)/100(%)]

Further where the functional group equivalent weight of the organopolysiloxane is not known, the MWg can be determined by the following expression by using a content rate (Csi) of the organopolysiloxane segment constituting the main chain and a molecular weight (MWox) of the poly(N-acylalkyleneimine) segment.

$$Mwg = \frac{Csi \times MWox}{100 - Csi}$$

The molecular weight (MWox) of the poly(N-acylalkyleneimine) segment can be calculated from a molecular weight and a degree of polymerization of the N-acylalkyleneimine unit, or can be measured by a gel permeation chromatography (GPC) method described later, but in the present invention, refers to a number-average molecular weight measured by the GPC method. The MWox of the modified organopolysiloxane is, from the viewpoint of being excellent in friction resistance, preferably 500 or more, more preferably 600 or more and even more preferably 700 or more, and preferably 5,500 or less, more preferably 3,500 or less and even more preferably 3,000 or less.

The weight-average molecular weight (MWsi) of the organopolysiloxane segment constituting the main chain is, from the viewpoint of being excellent in friction resistance, preferably 7,000 or more, more preferably 10,000 or more and even more preferably 20,000 or more, and preferably 120,000 or less, more preferably 80,000 or less and even more preferably 60,000 or less. Since the organopolysiloxane segment constituting the main chain has a skeleton common to that of the organopolysiloxane being the raw material compound, the MWsi is nearly equal to the weight-average molecular weight of the organopolysiloxane being the raw material compound. Here, the weight-average molecular weight of the organopolysiloxane being the raw material compound is measured by GPC in terms of polystyrene under the following condition.

Column: Super HZ4000+Super HZ2000 (manufactured by Tosoh Corp.)
Eluate: 1-mM trimethylamine/THF
Flow volume: 0.35 mL/min
Column temperature: 40° C.
Detector: UV
Sample: 50 μL The weight-average molecular weight (MWt) of the modified organopolysiloxane is preferably 10,000 or more, more preferably 12,000 or more and even more preferably 24,000 or more, and then preferably 200,000 or less, more preferably 150,000 or less, even more preferably 120,000 or less, further more preferably 92,000 or less and further more preferably 80,000 or less. Thereby, a coating is made which has a sufficient coating strength and is excellent in friction resistance. In the present description, the MWt can be determined from the weight-average molecular weight of the modified organopolysiloxane being the raw material compound and the above-mentioned mass ratio (α/β).

The modified organopolysiloxane can be produced by a well-known production method including, for example, methods disclosed in JP-A-2009-024114 and WO 2011/062210.

The urethane-based adhesive polymers include ones composed of a urethane resin obtained by reaction of a polyol with a polyisocyanate compound. Examples of the polyol include polyether polyols, polyester polyols, polycarbonate polyols and polycaprolactone polyols. Examples of the polyisocyanate compounds include diphenylmethane diisocyanate, tolylene diisocyanate and hexamethylene diisocyanate. Commercially available products of the urethane-based adhesive polymers include Baycusan C2000 (manufactured by Covestro AG).

The nonionic polymers are not especially limited, and any nonionic polymer can be used as long as it is usually used in the cosmetic field. The above-mentioned liquid agent can contain one or more nonionic polymers, and can further contain one or more anionic, cationic and/or amphoteric polymers in combination with the nonionic polymers.

Examples of the nonionic polymers include (meth)acrylic water-soluble nonionic polymers, (meth)acrylic water-insoluble nonionic polymers, polyvinylpyrrolidone, polyacrylamide, low-saponified polyvinyl alcohols (degree of saponification: 60 mol % or less), neutral polysaccharides and derivatives thereof (ethers, esters and the like thereof), and polyether. The neutral saccharides and derivatives thereof include neutral gums (guar gum, hydroxypropyl guar and the like), cellulose ethers (hydroxyethylcellulose (HEC), methylhydroxyethylcellulose (MHEC), ethylhydroxyethylcellulose (EHEC), methylethylhydroxyethylcellulose (MEHEC), hydroxypropylcellulose (HPC), hydroxypropylmethylcellulose (HPMC) and hydrophobized derivatives thereof (HM-EHEC and the like), and starches and derivatives thereof (dextrin and the like). The polyether include polyethylene glycol and polypropylene glycol.

Hereinafter, there are cited examples of compounds having an ethylenic unsaturated bond which can constitute the above-mentioned nonionic polymers such as (meth)acrylic water-soluble nonionic polymers, (meth)acrylic water-insoluble nonionic polymers, polyvinylpyrrolidone, polyacrylamide and low-saponified polyvinyl alcohols (degree of saponification: 60 mol % or less), but the present invention is not any more limited to the following specific examples.

Examples of nonionic monomers include (meth)acrylate esters such as methyl (meth)acrylate, ethyl (meth)acrylate, n-propyl (meth)acrylate, isopropyl (meth)acrylate, n-butyl (meth)acrylate, isobutyl (meth)acrylate, t-butyl (meth)acrylate, n-pentyl (meth)acrylate, n-hexyl (meth)acrylate, cyclohexyl (meth)acrylate, n-heptyl (meth)acrylate, n-octyl (meth)acrylate, 2-ethylhexyl (meth)acrylate, nonyl (meth) acrylate, decyl (meth)acrylate, dodecyl (meth)acrylate, phenyl (meth)acrylate, toluyl (meth)acrylate, benzyl (meth) acrylate), isobornyl (meth)acrylate, 2-methoxyethyl (meth) acrylate, 3-methoxybutyl (meth)acrylate, 2-hydroxyethyl (meth)acrylate, 2-hydroxypropyl (meth)acrylate, stearyl (meth)acrylate, glycidyl (meth)acrylate, 2-aminoethyl (meth)acrylate, γ-((meth)acryloyloxypropyl)trimethoxysilane, γ-((meth)acryloyloxypropyl)dimethoxymethylsilane, ethylene oxide adducts of (meth)acrylic acid, trifluoromethylmethyl (meth)acrylate, 2-trifluoromethylethyl (meth)acrylate, 2-perfluoroethylethyl (meth)acrylate, 2-perfluoroethyl-2-perfluorobutylethyl (meth)acrylate, 2-perfluoroethyl (meth)acrylate, perfluoromethyl (meth)acrylate, diperfluoromethylmethyl (meth)acrylate, 2-perfluoromethyl-2-perfluoroethylmethyl (meth)acrylate, 2-perfluorohexylethyl (meth)acrylate, 2-perfluorodecylethyl (meth)acrylate and 2-perfluorohexadecylethyl (meth)acrylate; aromatic alkenyl compounds such as styrene, α-methylstyrene, p-methylstyrene and p-methoxystyrene; cyanated vinyl compounds such as acrylonitrile and methacrylonitrile; conjugated dienic compounds such as butadiene and isoprene; halogen-containing unsaturated compounds such as vinyl chloride, vinylidene chloride, perfluoroethylene, perfluoropropylene and vinylidene fluoride; silicon-containing unsaturated compounds such as vinyltrimethoxysilane and vinyltriethoxysilane; unsaturated carboxylic anhydrides such as maleic anhydride; unsaturated dicarboxylate diesters such as dialkyl maleate and dialkyl fumarate; vinyl ester compounds such as vinyl acetate, vinyl propionate, vinyl pivalate, vinyl benzoate and vinyl cinnamate; maleimide compounds such as maleimide, N-methylmaleimide, N-ethylmaleimide, N-propylmaleimide, N-butylmaleimide, N-hexylmaleimide, N-octylmaleimide, N-dodecylmaleimide, N-stearylmaleimide, N-phenylmaleimide and N-cyclohexylmaleimide; monomers derived from (meth)acrylic acid or (meth)acrylamide and an alkylene oxide having 2 to 4 carbon atoms, such as polyethylene glycol (meth)acrylate, methoxypoly (ethylene glycol/propylene glycol) mono-(meth)acrylate, polyethylene glycol di(meth)acrylate and N-polyalkyleneoxy(meth)acrylamide; and hydrophilic nonionic monomers such as N-vinylpyrrolidone, N-(meth)acryloylmorpholine and acrylamide.

Among these, preferable is one or more selected from the group consisting of a (meth)acrylic water-insoluble nonionic polymer, polyvinylpyrrolidone and a low-saponified polyvinyl alcohol (degree of saponification: 60 mol % or less). Examples of commercially available products thereof include MAS 683 (manufactured by CosMED Pharmaceutical Co., Ltd.), Polyvinylpyrrolidone K-90 (manufactured by BASF AG) and JMR-150L (manufactured by Japan VAM & Poval Co., Ltd.).

Here, in the present description, the expression of "(meth) acryl" means "acryl or methacryl".

The anionic polymers are not especially limited, and any anionic polymer can be used as long as it is usually used in the cosmetic field. The above-mentioned liquid agent can contain one or more anionic polymers, and can further contain one or more nonionic, cationic and/or amphoteric polymers in combination with the anionic polymers.

Examples of the anionic polymers include anionic polysaccharides and derivatives thereof (alginate salts, pectin, hyaluronate salts and the like), anionic gums (xanthan gum, dehydroxanthan gum, hydroxypropylxanthan gum, gum arabic, karaya gum, gum tragacanth and the like), anionic cellulose derivatives (carboxymethylcellulose (CMC) and the like), (meth)acrylic water-soluble anionic polymers and acrylamide-based water-soluble anionic polymers.

Hereinafter, there are cited examples of compounds having an ethylenic unsaturated bond which can constitute the above-mentioned anionic polymers such as the (meth) acrylic water-soluble anionic polymers, but the present invention is not any more limited to the following specific examples. Examples of anionic monomers include unsaturated carboxylic acid compounds such as (meth)acrylic acid, maleic acid, maleic anhydride, itaconic acid, fumaric acid and crotonic acid; partial ester compounds of an unsaturated polybasic acid anhydride (for example, succinic anhydride or phthalic anhydride) with a hydroxyl-containing (meth) acrylate (for example, hydroxyethyl (meth)acrylate); compounds having a sulfonate group, such as styrenesulfonic acid and sulfoethyl (meth)acrylate; and compounds having a phosphate group, such as acid phosphooxyethyl (meth) acrylate. These anionic unsaturated monomers can be used as acids as they are, or by being partially neutralized or by being completely neutralized; or the anionic unsaturated monomers can also be partially neutralized or completely neutralized after being provided as acids as they are for copolymerization. Examples of basic compounds to be used for the neutralization include alkali metal hydroxides such as potassium hydroxide and sodium hydroxide, ammonia water, and amine compounds such as mono-, di- and triethanolamines and trimethylamine.

Among these, acrylic water-insoluble anionic polymers are especially preferable. Examples of commercially available products thereof include MASCOS 10 (manufactured by CosMED Pharmaceutical Co., Ltd.) and HiPAS 10 (manufactured by CosMED Pharmaceutical Co., Ltd.).

Further, an emulsifying thickener containing these nonionic polymer and anionic polymer can be used. Examples thereof include Polyacrylamide/(C13,C14)Isoparafin/Laureth-7 (Sepigel 305, manufactured by Seppic).

The cationic polymers are not especially limited, and any cationic polymer can be used as long as it is a cationic viscosity-thickening polymer usually used in the cosmetic field. The above-mentioned liquid agent can contain one or more cationic polymers, and can further contain one or more nonionic, anionic and/or amphoteric polymers in combination with the cationic polymers.

The cationic polymer is a polymer having a cationic group such as a quaternary ammonium group, or a group such as a primary, secondary or tertiary amino group, which can be ionized to a cationic group. The cationic polymer is typically a polymer having an amino group or an ammonium group on the side chain of the polymer chain, or a polymer containing a diallyl quaternary ammonium salt as its constituting unit.

Examples of preferable cationic polymers include cationized cellulose, cationic starch, cationic guar gum, vinylic or (meth)acrylic polymer or copolymers thereof having a quaternary ammonium side chain, quaternized polyvinylpyrrolidone, (meth)acrylate/aminoacrylate copolymers, amine-substituted poly(meth)acrylate cross polymers, (meth)acrylic water-soluble cationic polymers and acrylamide-based water-soluble cationic polymers.

Hereinafter, there are cited examples of compounds having an ethylenic unsaturated bond which can constitute the above-mentioned cationic polymers such as the (meth) acrylic water-soluble cationic polymers, but the present invention is not any more limited to the following specific examples. Examples of cationic monomers include ones made by cationizing N,N-dimethylaminoethyl (meth)acrylate, N,N-diethylaminoethyl (meth)acrylate, N,N-dimethylaminopropyl (meth)acrylate, N,N-diethylaminopropyl (meth)acrylate, N,N-dimethylaminoethyl (meth)acrylamide, N,N-diethylaminoethyl (meth)acrylamide, N,N-dimethylaminopropyl (meth)acrylamide, N,N-diethylaminopropyl (meth)acrylamide, p-dimethylaminomethylstyrene, p-dimethylaminoethylstyrene, p-diethylaminomethylstyrene, p-diethylaminoethylstyrene or the like, with a cationizing agent (for example, a halogenated alkyl such as methyl chloride, methyl bromide or methyl iodide, a dialkylsulfuric acid such as dimethylsulfuric acid, an epichlorohydrin adduct of a tertiary amine mineral acid salt such as N-(3-chloro-2-hydroxypropyl)-N,N,N-trimethylammonium chloride, an inorganic salt of hydrochloric acid, hydrobromic acid, sulfuric acid, phosphoric acid or the like, or a carboxylic acid such as formic acid, acetic acid or propionic acid).

Specific examples of the cationized cellulose include a polymer (polyquaternium-10) of a quaternary ammonium salt obtained by adding glycidyltrimethylammonium chloride to hydroxyethylcellulose, a hydroxyethylcellulose/dimethyldiallylammonium chloride copolymer (polyquaternium-4), and a polymer (polyquaternium-67) of a quaternary ammonium salt obtained by reacting hydroxyethylcellulose with a trimethylammonium-substituted epoxide and a lauryldimethylammonium-substituted epoxide.

Examples of the vinylic or (meth)acrylic polymers or copolymers thereof having a quaternary ammonium side chain include poly(2-methacryloxyethyltrimethylammonium chloride) (polyquaternium-37).

Specific examples of the quaternized polypyrrolidone include a quaternary ammonium salt (polyquaternium-11) synthesized from a copolymer of vinylpyrrolidone (VP) with dimethylaminoethyl methacrylate, and diethyl sulfate.

Examples of the (meth)acrylate/aminoacrylate copolymer include an (acrylate/aminoacrylate/C10-30 alkyl PEG-20 itaconic acid) copolymer.

Examples of the amine-substituted poly(meth)acrylate cross polymer include a polyacrylate-1 cross polymer and polyquaternium-52.

Among these, the acrylamide-based water-soluble cationic polymers are especially preferable. Examples of commercially available products thereof include a t-butylacrylamide/ethyl acrylate/dimethylaminopropylacrylamide/methoxypolyethylene glycol (meth)acrylate copolymer (RP77S, manufactured by Kao Corp.).

The amphoteric polymer is a polymer having both a cationic group and an anionic group. Speaking from the structural viewpoint, the amphoteric polymer can be derived by introducing an anionic group or a comonomer having an anionic group to any one of the above-mentioned cationic polymers.

As the amphoteric polymer, any amphoteric polymer can be used as long as it is an amphoteric polymer usually used in the cosmetic field. The above-mentioned liquid agent can contain one or more amphoteric polymers, and can further contain nonionic, anionic and/or cationic polymers in combination with the amphoteric polymers.

Examples of the amphoteric polymers include carboxyl-modified or sulfonate-modified cationic polysaccharides (carboxymethylchitosan and the like), (meth)acrylate-based polymers having a phosphobetaine group or a sulfobetaine group on their side chain, and (meth)acrylic amphoteric polymers.

Hereinafter, there are cited examples of compounds having an ethylenic unsaturated bond which can constitute the above-mentioned amphoteric polymers such as the (meth) acrylic amphoteric polymers, but the present invention is not any more limited to the following specific examples. Examples of amphoteric monomers include compounds obtained by causing a modifying agent such as sodium or potassium haloacetate to act on an above-mentioned specific example of the cationic monomer precursors. Further, specific examples of polarizing monomers include oxidized amine compounds of N,N-dimethylaminoethyl (meth)acrylate, N,N-diethylaminoethyl (meth)acrylate, N,N-dimethylaminopropyl (meth)acrylate, N,N-diethylaminopropyl (meth)acrylate, N,N-dimethylaminoethyl(meth)acrylamide, N,N-diethylaminoethyl (meth)acrylamide, N,N-dimethylaminopropyl (meth)acrylamide, N,N-diethylaminopropyl (meth)acrylamide, N,N-dimethylaminovinyl propionate, p-dimethylaminomethylstyrene, p-dimethylaminoethylstyrene, p-diethylaminomethylstyrene, p-diethylaminoethylstyrene or the like.

Other examples thereof include copolymers (dimethylallylammonium chloride/acrylic acid copolymer (polyquaternium-22) and the like) of a cationic vinylic or (meth)acrylic monomer with (meth)acrylic acid.

As the (c) adhesive polymer, from the viewpoint of fixation of solid materials by a coating and improvement of followability of the coating to movements of skin, an adhesive polymer good in adhesiveness is selected. As the adhesive polymer, a polymer is preferable which has a maximum tensile shearing load of 1 N or more as measured by reference to JIS K6850; a polymer of 3 N or more is more preferable; and a polymer of 5 N or more is even more preferable. From the viewpoint of securing adhesiveness of more cubic decorations, a polymer of 8 N or more is further more preferable. The maximum tensile shearing load is preferably 200 N or less, more preferably 150 N or less and even more preferably 100 N or less.

Specifically, it is preferable to use one or more selected from the group consisting of the rubber-based adhesive polymer, the silicone-based adhesive polymer, the acrylic adhesive polymer and the urethane-based adhesive polymer; and then, it is preferable to use at least one selected from the group consisting of the nonionic polymer, the anionic polymer, the cationic polymer and the amphoteric polymer.

The adhesiveness (maximum tensile shearing load) of the polymer can be measured as follows. 20 mg of a polymer solution (10% ethanol solution or saturated solution) is applied to a region of 1.25 cm×2.5 cm of one end of one sheet of a polycarbonate substrate (manufactured by Standard Test Piece, Carboglass Polish Clear, 10 cm×2.5 cm×2.0 cm), and laminated with another sheet of the polycarbonate substrate, and dried for 12 hours or more. Both ends of the polycarbonate substrates were pulled by using a Tensilon UTC-100W, manufactured by Orientec Co., Ltd. at a tensile rate of 5 mm/min to measure the maximum tensile shearing load.

The content of the (c) adhesive polymer in the composition Y is, from the viewpoint of stable fixation of solid materials and improvement of followability of a coating to movements of skin, preferably 0.1% by mass or more and 20% by mass or less. The content is more preferably 0.2% by mass or more, even more preferably 0.5% by mass or more, further more preferably 1% by mass or more and further more preferably 5% by mass or more. Then the content is more preferably 15% by mass or less, even more preferably 12% by mass or less and further more preferably 10% by mass or less. Specifically, the content is preferably 0.1% by mass or more and 20% by mass or less, more preferably 0.2% by mass or more and 15% by mass or less, even more preferably 0.5% by mass or more and 12% by mass or less, further more preferably 1% by mass or more and 12% by mass or less and further more preferably 5% by mass or more and 10% by mass or less.

The component (d) to be used in the composition Y is an oil. The incorporation of the component (d) improves friction resistance of a coating, stable fixation of solid materials and followability of the coating to movements of skin. The component (d) includes one or more selected from the group consisting of a liquid oil (an oil liquid at 20° C.) and a solid oil (an oil solid at 20° C.)

The liquid oil in the present invention is an oil liquid at 20° C., and includes semi-solid ones having flowability. The liquid oil includes hydrocarbon oils, ester oils, higher alcohols, silicone oils and fatty acids. Among these, from the viewpoint of smoothness in application, friction resistance of a coating, stable fixation of solid materials, followability of the coating to movements of skin, and usage feeling, preferable are hydrocarbon oils, ester oils and silicone oils. Further one or more, in combination, selected from these liquid oils may be used.

The liquid hydrocarbon oil includes liquid paraffin, squalane, squalene, n-octane, n-heptane, cyclohexane, light isoparaffin, liquid isoparaffin, hydrogenated polyisobutene, polybutene and polyisobutene; and from the viewpoint of usage feeling, preferable are liquid paraffin, light isoparaffin, liquid isoparaffin, squalane, squalene, n-octane, n-heptane and cyclohexane; and more preferable are liquid paraffin and squalene. The viscosity at 30° C. of the hydrocarbon oil is, from the viewpoint of scratch resistance and extensibility of an electrostatically sprayed coating, preferably 1 mPa·s or more and more preferably 3 mPa·s or more. Then the content of the total of isodecane, isohexadecane and hydrogenated polyisobutene in the liquid agent is, from the viewpoint of scratch resistance and extensibility of a coating, preferably 10% by mass or less, more preferably 5% by mass or less, even more preferably 1% by mass or less and further more preferably 0.5% by mass or less; and the liquid agent may not contain these.

The viscosity at 30° C. of the ester oil and the silicone oil is, similarly from the viewpoint of scratch resistance and extensibility of an electrostatically sprayed coating, preferably 1 mPa·s or more and more preferably 3 mPa·s or more.

The viscosity used here is measured at 30° C. by a BM-type viscometer (manufactured by Tokyo Keiki Inc., measuring condition: rotor, No. 1, 60 rpm, for 1 min). From the similar viewpoint, the content of the total of the ether oils such as cetyl-1,3-dimethylbutyl ether, dicapryl ether, dilauryl ether and diisostearyl ether in the liquid agent is preferably 10% by mass or less, more preferably 5% by mass or less and even more preferably 1% by mass or less.

The ester oils include esters composed of a straight-chain or branched-chain fatty acid and a straight-chain or branched-chain alcohol or polyhydric alcohol. Specific examples thereof include isopropyl myristate, cetyl isooctanoate, isocetyl octanoate, octyldodecyl myristate, isopropyl palmitate, butyl stearate, hexyl laurate, decyl oleate, octyldodecyl oleate, hexyldecyl dimethyloctanoate, cetyl lactate, myristyl lactate, lanolin acetate, isocetyl stearate, isocetyl isostearate, ethylhexyl isononanoate, isononyl isononanoate, isotridecyl isononanoate, isostearyl isostearate, cholesteryl 12-hydroxystearate, ethylene glycol di-2-ethylhexanoate, a dipentaerythritol fatty acid ester, N-alkyl glycol mono-isostearate, propylene glycol dicaprylate, propylene glycol diisostearate, neopentyl glycol dicaprylate, diisostearyl malate, glycerol di-2-heptylundecanoate, trimethylolpropane tri-2-ethylhexanoate, trimethylolpropane triisostearate, pentaerythrit tetra-2-ethylhexanoate, glyceryl tri-2-ethylhexanoate, trimethylolpropane triisostearate, cetyl 2-ethylhexanoate, 2-ethylhexyl palmitate, diethylhexyl naphthalenedicarboxylate, C12 to 15 alkyl benzoate, stearyl isononanoate, glyceryl tri(caprylate/caprate), butylene glycol (dicaprylate/caprate), propylene glycol di(caprylate/caprate), glyceryl triisostearate, glyceryl tri-2-heptylundecanoate, a tri-coconut oil fatty acid glyceryl ester, a castor oil fatty acid methyl ester, oleyl oleate, 2-heptylundecyl palmitate, diisobutyl adipate, an N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, di-2-ethylhexyl succinate, triethyl citrate, 2-ethylhexyl paramethoxycinnamate and tripropylene glycol dipivalate.

Among these, from the viewpoint of making an electrostatically sprayed coating to closely adhere on a skin and being excellent in feeling when the coating is applied to the skin, preferable is one selected from the group consisting of octyldodecyl myristate, isocetyl stearate, isononyl isononanoate, isocetyl isostearate, stearyl isononanoate, diisobutyl adipate, di-2-ethylhexyl sebacate, isopropyl myristate, isopropyl palmitate, diisostearyl malate, neopentylglycol dicaprate and glycerol tri(caprylate/caprate); more preferable is at least one selected from the group consisting of isopropyl myristate, isopropyl palmitate, diisostearyl malate, neopentyl glycol dicaprate, C12-15 alkyl benzoate and glycerol tri(caprylate/caprate); and even more preferable is at least one selected from the group consisting of neopentylglycol dicaprate and glycerol tri(caprylate/caprate).

As the ester oil, plant oils and animal oils containing the above ester oils can be used. Examples thereof include olive oil, jojoba oil, macadamia nut oil, meadowfoam oil, castor oil, safflower oil, sunflower seed oil, avocado oil, canola oil, apricot kernel oil, rice embryo oil and rice bran oil.

The higher alcohols include liquid higher alcohols having 12 to 20 carbon atoms; preferable are higher alcohols containing a branched fatty acid as a constituent; and the higher alcohols specifically include isostearyl alcohol and oleyl alcohol.

The liquid silicone oils include straight-chain silicones, cyclic silicones and modified silicones, and examples thereof include dimethylpolysiloxane, dimethylcyclopolysiloxane, methylphenylpolysiloxane, methylhydrogenpolysiloxane, phenyl-modified silicones and higher alcohol-modified organopolysiloxanes. The content of the silicone oil in the component (d) is, from the viewpoint of adhesiveness to skin, preferably 35% by mass or less, and is, from the viewpoint of improving peelability, more preferably 10% by mass or less, even more preferably 1% by mass or less and further more preferably 0.1% by mass or less.

The kinematic viscosity at 25° C. of the silicone oil is, from the viewpoint of friction resistance of an electrostatically sprayed coating, fixation of solid materials and followability of the coating to movements of skin, preferably 3 mm$^2$/s or more, more preferably 4 mm$^2$/s or more and even more preferably 5 mm$^2$/s or more, and preferably 30 mm$^2$/s or less, more preferably 20 mm$^2$/s or less and even more preferably 10 mm$^2$/s or less.

Among these, from the viewpoint of friction resistance of an electrostatically sprayed coating, fixation of solid materials and followability of the coating to movements of skin, it is preferable that the silicone oil contain dimethylpolysiloxane.

Further, an oil solid at 20° C. (solid oil) also can be used. The oil solid at 20° C. exhibits a property of solid at 20° C., and one having a melting point of 40° C. or more is preferable. The oil solid at 20° C. includes hydrocarbon waxes, ester waxes, paraoxybenzoate esters, higher alcohols, esters of straight-chain fatty acid having 14 or more carbon atoms, triglycerides containing three straight-chain fatty acids having 12 or more carbon atoms as constituents and silicone waxes; and the solid oil can contain one or more selected from these. Such waxes are not limited as long as being ones used for usual cosmetics; and examples thereof include mineral waxes such as ozokerite and ceresin; petroleum waxes such as paraffin, microcrystalline waxes and petrolatum; synthetic hydrocarbon waxes such as Fischer-Tropsh waxes and polyethylene waxes; plant waxes such as carnauba wax, candellila wax, rice wax, Japan wax, sunflower wax and hydrogenated jojoba oil; animal waxes such as beeswax and whale wax; synthetic waxes such as silicone wax, fluorine-based wax and synthetic beeswax; and fatty acids, higher alcohols and derivatives thereof. Further the paraoxybenzoate esters include methyl paraoxybenzoate, ethyl paraminobenzoate, isobutyl paraoxybenzoate, isopropyl paraoxybenzoate, ethyl paraoxybenzoate, butyl paraoxybenzoate, propyl paraoxybenzoate and benzyl paraoxybenzoate; and the triglycerides containing three straight-chain fatty acids having 12 or more carbon atoms as constituents include glyceryl trilaurate, glyceryl trimyristate, glyceryl tripalmitate and glyceryl tribehenate. The fatty acid ester oils having straight-chain fatty acid having 14 or more carbon atoms as constituents include myristyl myristate.

The content of the component (d) in the composition Y is, from the viewpoint of stable fixation of solid materials, followability of a coating to movements of skin and usage feeling, preferably 2% by mass or more and 100% by mass or less, more preferably 3% by mass or more and 100% by mass or less and even more preferably 5% by mass or more and 100% by mass or less; and in the concurrent use with the component (c), the content is preferably 3% by mass or more and 80% by mass or less, preferably 5% by mass or more and 60% by mass or less and preferably 5% by mass or more and 50% by mass or less. Among these, the content of the liquid oil in the component (d) is preferably 5% by mass or more and 100% by mass or less, more preferably 10% by mass or more and 100% by mass or less, even more preferably 20% by mass or more and 100% by mass or less and further more preferably 30% by mass or more and 100% by mass or less. The content of the solid oil is preferably 90% by mass or less, more preferably 80% by mass or less and even more preferably 70% by mass or less.

The composition Y contains one or more selected from the group consisting of the component (c) and the component (d), but from the viewpoint of stable fixation of solid materials, followability of a coating to movements of skin and usage feeling, it is preferable that the composition Y contain both.

The composition Y may further contain a component (e), a polyol. The polyol of the component (e) is preferably a liquid at 20° C. Examples of the polyol of the component (e) include alkylene glycols such as ethylene glycol, propylene glycol, 1,3-propanediol and 1,3-butanediol; dialkylene glycols such as diethylene glycol and dipropylene glycol; polyethylene glycol having a weight-average molecular weight of 2,000 or less; and glycerols such as glycerol, diglycerol and triglycerol. Among these, from the viewpoint of stable fixation of solid materials and followability of a coating to movements of skin, preferable are ethylene glycol, propylene glycol, 1,3-butanediol, dipropylene glycol, polyethylene glycol having a weight-average molecular weight of 1,000 or less, glycerol and diglycerol; and more preferable are propylene glycol, 1,3-butanediol and glycerol; and even more preferable is glycerol.

The content of the polyol in the composition Y is, from the viewpoint of stable fixation of solid materials and followability of a coating to movements of skin, preferably 40% by mass or less, more preferably 30% by mass or less, even more preferably 25% by mass or less and further more preferably 20% by mass or less.

Then, the total of the contents of the component (d) and the component (e), (d+e), is, from the viewpoint of stable fixation of solid materials and followability of a coating to movements of skin, preferably 8% by mass or more, more preferably 10% by mass or more and even more preferably 15% by mass or more, and preferably 100% by mass or less; and for concurrent use with the component (c), the total content is preferably 80% by mass or less and more preferably 50% by mass or less.

The composition Y may contain, in addition to the above components, a surfactant, a pH regulator, a chelating agent, a thickener other than the adhesive polymer, a fragrance, a coloring matter, a blood circulation accelerator, a cool sensation agent, an antiperspirant, a skin activator, a moisturizer, a refrigerant, a UV protective agent, a repellant, an antioxidant, a stabilizer, various vitamins, ethanol, and the like. The surfactant includes nonionic surfactants, cationic surfactants, anionic surfactants and amphoteric surfactants.

The step (step C) of applying the composition Y to a skin surface may be before the step A) or may be after the step B). A unit of applying the composition Y to a skin surface may be any unit as long as being a unit other than electrostatic spraying. The unit includes a unit of applying to a skin surface by a finger or the like, and a unit of applying to a skin surface by using an applicator.

Then, the step D) will be described.

The step D) is a step of affixing a nanofiber sheet on a skin surface. Here, the nanofiber sheet is a sheet fabricated by discharging a coating-formable polymer-containing liquid on a substrate with an electrostatic apparatus. As such a nanofiber sheet, preferable is one fabricated by spraying the composition X on a substrate by an electrostatic apparatus. Here, it is preferable that the composition X to be used for fabrication of the nanofiber sheet and a fabrication method thereof be similar to those of the step B) described before.

In a method for producing a wearable coating having the step D), the step A) and then the step D) are carried out, and the step B) is carried out after the step D) or before the step A).

The method for producing a wearable coating according to the present invention may comprise, in addition to the step A), the step B) and the step C) or the step A), the step D) and the step B), G) a step of applying a foundation to a skin surface.

A powder to be used for the foundation of the step G) includes coloring pigments, extender pigments and organic powder. The coloring pigments include inorganic coloring pigments, organic coloring pigments and organic coloring matters, and one or more thereof can be used.

The inorganic coloring pigments specifically include inorganic colored pigments such as red ocher, iron hydroxide, iron titanate, yellow iron oxide, black iron oxide, carbon black, Berlin blue, ultramarine blue, Berlin blue titanium oxide, black titanium oxide, titanium-titanium oxide sintered material, manganese violet, cobalt violet, chromium oxide, chromium hydroxide, cobalt oxide and cobalt titanate; and inorganic white pigments such as titanium oxide, zinc oxide, calamine, zirconium oxide, magnesium oxide, cerium oxide, aluminum oxide and composites thereof. One or more thereof can be used.

Among these, preferable is one or more selected from the group consisting of iron oxide, titanium oxide and zinc oxide; and more preferable is one or more selected from the group consisting of titanium oxide, zinc oxide, red ocher, yellow iron oxide and black iron oxide.

The organic coloring pigments and organic coloring matters include organic tar pigments such as Red No. 3, Red No. 102, Red No. 104, Red No. 106, Red No. 201, Red No. 202, Red No. 204, Red No. 205, red No. 220, Red No. 226, red No. 227, Red No. 228, Red No. 230, Red No. 401, Red No. 405, Red No. 505, Orange No. 203, Orange No. 204, Orange No. 205, Yellow No. 4, Yellow No. 5, Yellow No. 401, Blue No. 1 and Blue No. 404; and organic coloring matters such as β-carotene, caramel and paprika coloring matter. Further, those covered with a polymer such as a cellulose or a polymethacrylate ester, and the like are included. Among these, it is preferable that at least Red No. 102 be contained.

The extender pigments include barium sulfate, calcium sulfate, magnesium sulfate, magnesium carbonate, calcium carbonate, talc, mica, kaolin, sericite, silicic acid, silicic acid anhydride, aluminum silicate, magnesium silicate, aluminum magnesium silicate, calcium silicate, barium silicate, strontium silicate, tungstic acid metal salts, hydroxyapatite, vermiculite, clay, bentonite, montmorillonite, hectorite, smectite, zeolite, ceramic powder, dibasic calcium phosphate, alumina, silica, aluminum hydroxide, boron nitride, synthetic mica, synthetic sericite, metallic soap, and barium sulfate-treated mica. One or more thereof can be used.

Among these, it is preferable that barium sulfate, calcium carbonate, mica, silicic acid anhydride, talc, boron nitride or synthetic mica be contained.

The organic powder includes silicone rubber powder, silicone resin-covered silicone rubber powder, polymethylsilsesquioxane powder, polyamide powder, nylon powder, polyester powder, polypropylene powder, polystyrene powder, polyurethane powder, vinyl resin powder, urea resin powder, phenol resin powder, fluororesin powder, silicone resin powder, acrylate resin powder, melamine resin powder, polycarbonate resin powder, divinylbenzene-styrene copolymer powder, silk powder, wool powder, cellulose powder, long chain-alkylphosphoric acid metal salt powder, N-mono-long chain-alkylacyl basic amino acid powder, and composite thereof. One or more thereof can be used.

Among these, it is preferable that cellulose powder, silicone rubber powder, silicone resin-covered silicone rubber powder, polymethylsilsesquioxane powder, acrylate resin powder or nylon powder be contained.

As a powder to be used for the foundation of the step (G), any one of the above can be used as it is, and one or more of the powders having been subjected to a hydrophobization treatment can be used. The hydrophobization treatment is not limited as long as it is a treatment carried out for usual cosmetic powders, and suffices if a dry treatment, a wet treatment or the like is carried out by using a surface treating agent such as a fluorocompound, a silicone-based compound, a metallic soap, an amino acid-based compound, lecithin, an alkyl silane, an oil or an organotitanate.

As a powder to be used for the foundation of the step (G), one or more of the powders having been subjected to a hydrophilization treatment can also be used. The hydrophilization treatment is not limited as long as it is a treatment carried out for usual cosmetic powders.

For powders, as long as they are usually used for cosmetics, powders having a spherical, plate-like, needle-like or indeterminate shape, a fusiform, a microparticulate shape, powders having a particle diameter such as a pigment-class, and/or powders having a porous or nonporous particulate structure can be used.

The average particle diameter of the powder contained in the foundation of the step (G) is, from the viewpoint of uniform close adhesion to skin hillocks, skin grooves and pores, and impartation of natural cosmetic feeling, preferably 0.001 μm or more and 200 μm or less, more preferably 0.01 μm or more and 50 μm or less, even more preferably 0.02 μm or more and 20 μm or less and further more preferably 0.05 μm or more and 10 μm or less.

In the present invention, the average particle diameter of the powder to be used for the foundation of the step (G) is measured by an electron microscope and a particle size distribution analyzer using a laser diffraction/scattering method. Specifically, in the laser diffraction/scattering method, ethanol is used as a disperse medium and the measurement is carried out by a laser diffraction scattering type particle size distribution analyzer (for example, LMS-350, manufactured by Seishin Enterprise Co., Ltd.). Here, where the powder has been subjected to the hydrophobization treatment or the hydrophilization treatment, the average particle diameter and the content of the component (c) mean an average particle diameter and a mass including those of the powder having been subjected to the hydrophobization treatment or the hydrophilization treatment.

One or more of the powders can be used for the foundation of the step (G); and the content thereof in the foundation is, though depending on the form of the foundation, from the viewpoint of finishing, preferably 1% by mass or more, more preferably 3% by mass or more and even more preferably 5% by mass or more, and preferably 95% by mass or less and more preferably 90% by mass or less. Then the content thereof in the foundation is preferably 1% by mass or more and 95% by mass or less, more preferably 3% by mass or more and 90% by mass or less and even more preferably 5% by mass or more and 90% by mass or less.

The foundation to be used in the step G) has a color similar to that of a human skin for the foundation to be applied to, or is transparent or translucent, and is applied and spread to the entirety of the application site; and the color difference E between the applied and spread site and sites neighboring the site is made to be 2 or less.

Then, the form of the foundation is not especially limited, and there is allowed any type of a powder type, a solid powder type, a liquid type, an oily type, an emulsion type and an oily solid type. Then, in the step (G), the coloring pigment and the like are applied together with a solvent or an adhesive component to skin, and are applied without gaps and continuously to the skin; and patterns and formative application are excluded.

Components other than the powders contained in the foundation to be used in the step G) include oils (including liquid oils and solid oils), emulsifiers, water-soluble polymers, fragrances, repellants, antioxidants, stabilizers, antiseptics, thickeners, pH regulators, blood circulation accelerators, various vitamins, cool sensation agents, antiperspirants, germicides, skin activators and moisturizers.

The application of the foundation of the step G) may be carried out by a usual application unit according to the kind of a cosmetic, and the application unit includes application by spreading or pressing the foundation, for example, by using a finger or the palm of a hand, and application by spreading or pressing the foundation, for example, by using a dedicated tool. The cosmetic of the step G) is a composition different from the composition X and the composition Y, and is different also from the solid materials of the step A).

Specific examples of the method for producing a wearable coating of the present invention will be described. First, a method comprising the step B) includes (1) a mode in which the step A), the step B) and then the step C) are carried out and (2) a mode in which the step C), the step A) and then the step B) are carried out. Further, these steps may be carried out multiple times. Therefore, the method includes the following modes in which the steps are carried out as follows: (1) the step B), the step C), the step A), the step B) and then the step C) or a step of applying a cosmetic containing water or an oil in this order; (2) the step C), the step B), the step A), the step B) and then the step C) in this order; (3) the step B), the step C), the step A), the foundation step (step G), the step B) and then the step C) in this order; or (4) the step B), the step C), the foundation step (step G), the step A), the step B) and then the step C) in this order.

In the second step C) carried out after the step B), there may be applied a composition Y2, different from the composition Y but nearly similar thereto, in which one or more selected from the component (c) and the component (d) are contained. There may be cases, where in the first step C), the composition Y, which contains the component (c) and the component (d), is applied and in the second step C), a composition Y2, in which no component (c) is contained but the component (d) is contained, is applied, or where the kinds and contents of the component (c) and the component (d) are different between the composition Y and the composition Y2.

Further a method comprising the step D) includes a mode in which the step B) in the method comprising the step B) is replaced by the step D), and further includes a mode in which part of the steps B) is replaced by the step D).

According to the present invention, the application range of the composition Y is equal to or broader than the application range of the composition X; and the solid materials of the step A) are disposed partially in the application range of the composition X. Therefore, the layer structure has a region where only the composition X and the composition Y are laminated, and partially regions where the composition X, the composition Y and the solid materials of the step A) are laminated.

Then, where the solid materials are cubic, the composition X can also be applied to a region where the solid materials contact with a skin. Where the solid materials are flat, powdery or granular, it is preferable that a layer of the composition X be present across the entirety of the solid materials.

The present invention relates further to a method for producing a wearable coating on skin, the method comprising:

B) a step of electrostatically spraying a composition X comprising the following component (a) and the following component (b) directly on skin to thereby form a coating on a skin surface:
  (a) one or more volatile substances selected from the group consisting of water, an alcohol, and a ketone, and
  (b) a polymer having a coating forming ability;
C) a step of applying a composition Y, other than the composition X, comprising one or more components selected from the group consisting of the following component (c) and the following component (d) to the skin:
  (c) an adhesive polymer, and
  (d) an oil;
E) a step of, after the step C), applying a wearable article having a color different from a skin color partially to a region having the coating formed thereon; and
F) a step of, after the step E), electrostatically spraying the composition X to thereby form a coating on a broad region containing the worn region.

Here, the step B) and the step C) are the same as in the above.

The step E) is a step of applying a wearable article having a color different from a skin color partially to a region having the coating formed thereon. In the step of the partial application to the skin, from the viewpoint of suppressing an influence on the coating made before, an applying method using air brushing, spraying or stamping is preferable. Here, a wearable article having a color different from a skin color refers to a wearable article having a color clearly different from a skin color. More specifically, the color difference E between the skin and the wearable article represented by the following expression is 3 or more, and more preferably 5 or more.

$$\Delta E = (\Delta a^2 + \Delta b^2 + \Delta L^2)^{1/2} \quad \text{(Expression 1)}$$

where a, b and L are based on the CIE colorimetric system.

More specifically, the application unit includes a unit of painting a decoration using a color clearly different from a skin color, on the coating. Here, the decoration is in such a state that a borderline of the color different from a skin color is formed of a combination of curves and straight lines, preferably of a plurality of lines, and there is included the case where the borderline displays a picture, a letter, a pattern or the like.

The step F) is a step carried out after the step E), and is a step of again electrostatically spraying the composition X to thereby form a coating on a broad region containing the worn region. The step F) fixes the wearable article of the step E) and improves friction resistance of the coating and also improves followability to movements of the skin.

According to the method of the present invention, the coating stably fixes the wearable article and paints composed of solid materials on skin and causes no pressure feeling or uncomfortable feeling to the skin, has excellent compatibility with movements of the skin and is excellent also in peelability after usage.

Further the edge of the formed coating is hardly visually recognized and even when the solid materials have protrusions, it is possible to prevent production of gaps between the solid materials and the film obtained by electrostatic spraying. The coating of the film obtained by electrostatic spraying is translucent or transparent and therefore excellent in decorativeness. The film is easy to peel gently, and therefore it is excellent in peelability. The wearable coating can be prevented from being peeling off, even if it is sprayed with water or the like, and moreover the wearable coating can cause little irritation to the skin.

Pertaining to the above-mentioned embodiment, the present invention further discloses the following production methods, compositions and methods for use of the coatings.

<1> A method for producing a wearable coating having a solid material fixed on skin, the method comprising:
A) a step of placing one or more solid materials selected from the group consisting of a powder, a granule, a film, a fiber, a flat material, and a cubic material other than these, on a skin surface;
B) a step of, after the step A), electrostatically spraying a composition X comprising the following component (a) and the following component (b) directly on the skin to thereby form a coating on the skin surface:
(a) one or more volatile substances selected from the group consisting of water, an alcohol, and a ketone, and
(b) a polymer having a coating forming ability; and after the step B) or before the step A),
C) a step of applying a composition Y, other than the composition X, comprising one or more components selected from the group consisting of the following component (c) and the following component (d) to the skin:
(c) an adhesive polymer, and
(d) an oil.

<2> A method for producing a wearable coating having a solid material fixed on skin, the method comprising:
A) a step of placing one or more solid materials selected from the group consisting of a powder, a granule, a film, a fiber, and a flat material other than these, on a skin surface;
D) a step of affixing a nanofiber sheet on the skin surface; and after the step D) or before the step A),
C) a step of applying a composition Y, other than the composition X, comprising one or more components selected from the group consisting of the following component (c) and the following component (d) to the skin:
(c) an adhesive polymer, and
(d) an oil.

<3> A method for producing a wearable coating on skin, the method comprising:
B) a step of electrostatically spraying a composition X comprising the following component (a) and the following component (b) directly on the skin to thereby form a coating on a skin surface:
(a) one or more volatile substances selected from the group consisting of water, an alcohol, and a ketone, and
(b) a polymer having a coating forming ability;
C) a step of applying a composition Y, other than the composition X, comprising one or more components selected from the group consisting of the following component (c) and the following component (d) to the skin:
(c) an adhesive polymer, and
(d) an oil; and
E) a step of, after the step C), applying a decoration having a color different from a skin color partially to a region having the coating formed thereon to the skin.

<4> The method for producing a wearable coating on skin according to <3>, further comprising F) a step of, after the step E), electrostatically spraying the composition X to thereby form a coating on a broad region containing the worn region.

<5> The method according to <1> or <2>, wherein the step A) is a step of placing each of a plurality of solid materials discontinuously on the skin surface.

<6> The method according to <1> or <2>, wherein the step A) is a step of placing the solid materials on the skin surface by scattering or mounting.

<7> The method according to any one of <1> to <6>, wherein the composition Y is a composition comprising (c) an adhesive polymer.

<8> The method according to any one of <1> to <7>, wherein the composition Y is a composition comprising (c) an adhesive polymer and (d) an oil.

<9> The method according to any one of <1> to <8>, wherein the component (c) in the composition Y is an adhesive polymer having a maximum tensile shearing load of 1 N or more.

<10> The method according to any one of <1> to <9>, wherein the step C) is a step of applying the composition Y to the skin by using a unit other than electrostatic spraying.

<11> The method according to any one of <1> to <10>, wherein the composition Y further comprises a polyol.

<12> The method according to any one of <1> to <11>, wherein the coating formed by electrostatic spraying in the step B) is a porous coating.

<13> The method according to any one of <1> to <12>, wherein the step B) is a step of electrostatically spraying the composition X on the skin by using an electrostatic spray apparatus to thereby form a coating made of a deposit of a fiber, the electrostatic spray apparatus comprising a container for accommodating the composition X, a nozzle for discharging the composition X, a feed device for feeding the composition X accommodated in the container to the nozzle, and a power source for applying a voltage to the nozzle.

<14> The method according to <1>, comprising carrying out the step B), the step C), the step A), the step B) and then the step C) in this order; the step C), the step B), the step A), the step B) and then the step C) in this order; the step B), the step C), the step A), a foundation step, the step B) and then the step C) in this order; or the step B), the step C), a foundation step, the step A), the step B) and then the step C) in this order;

<15> The method according to <2>, wherein one or more of the steps B) are each altered to the step D).

<16> The method according to <4>, comprising, between the step E) and the step F), A) a step of placing one or more solid materials selected from the group consisting of a powder, a granule, a film, a fiber, a flat material, and a cubic material other than these, on the skin surface.

<17> The method according to <3> or <4>, wherein the decoration having a color different from a skin color has a color difference E, represented by the following expression, between the skin and the decoration of 3 or more.

$$\Delta E = (\Delta a^2 + \Delta b^2 + \Delta L^2)^{1/2} \qquad \text{(Expression 2)}$$

where a, b and L are based on the CIE colorimetric system.

<18> The method according to any one of <1> to <17>, wherein it is preferable that the (c) adhesive polymer be one or more selected from the group consisting of a rubber-based adhesive polymer, a silicone-based adhesive polymer, an acrylic adhesive polymer and a urethane-based adhesive polymer; and it is preferable that the (c) adhesive polymer be at least one selected from the group consisting of a nonionic polymer, an anionic polymer, a cationic polymer and an amphoteric polymer.

<19> The method according to any one of <1> to <18>, wherein the adhesive polymer is preferably a polymer having a maximum tensile shearing load of 1 N or more, more preferably a polymer of 3 N or more and even more preferably a polymer of 5 N or more.

<20> The method according to any one of <1> to <19>, wherein the content of the (c) adhesive polymer in the composition Y is preferably 0.1% by mass or more and 20% by mass or less, more preferably 0.2% by mass or more and 15% by mass or less, even more preferably 5% by mass or more and 12% by mass or less and further more preferably 5% by mass or more and 10% by mass or less.

<21> The method according to any one of <1> to <20>, wherein the content of the component (d) in the composition Y is preferably 2% by mass or more and 100% by mass or less, more preferably 3% by mass or more and 100% by mass or less and even more preferably 5% by mass or more and 100% by mass or less.

<22> The method according to any one of <1> to <21>, wherein it is preferable that the component (d) of the composition Y comprise one or more selected from the group consisting of a liquid oil (an oil liquid at 20° C.) and a solid oil (an oil solid at 20° C.)

<23> The method according to <22>, wherein the liquid oil (the oil liquid at 20° C.) is one or more selected from the group consisting of a hydrocarbon oil, an ester oil, a plant oil, a higher alcohol, a silicone oil and a fatty acid.

<24> The method according to <22> or <23>, wherein the oil solid at 20° C. is one or more selected from the group consisting of a hydrocarbon wax, an ester wax, a paraoxybenzoate ester, a higher alcohol, an ester of a straight-chain fatty acid having 14 or more carbon atoms, a triglyceride containing three straight-chain fatty acids having 12 or more carbon atoms as constituents and a silicone wax.

EXAMPLES

Hereinafter, the present invention will be described in more detail by way of Examples. However, the scope of the present invention is not limited to these Examples. Unless otherwise specified, "%" means "mass %".

Synthesis Example 1 (Production of a poly(N-propionylethyleneimine)-Modified Silicone)

19.0 g (0.12 mol) of diethyl sulfate and 81.0 g (0.82 mol) of 2-ethyl-2-oxazoline were dissolved in 203.0 g of dehydrated ethyl acetate, and heated and refluxed in a nitrogen atmosphere for 8 hours to thereby synthesize a terminal-reactive poly(N-propionylethyleneimine). The number-average molecular weight was measured by GPC, and was 1,100. Thereto, a 33% ethyl acetate solution of 300 g of a side chain-primary aminopropyl-modified polydimethylsiloxane (weight-average molecular weight: 32,000, amine equivalent: 2,000) was collectively added, and heated and refluxed for 10 hours. The reaction mixture was concentrated under reduced pressure to thereby obtain an N-propionylethyleneimine-dimethylsilozane copolymer as a light yellow rubbery solid (390 g, yield: 97%). The content rate of an organopolysiloxane segment in the final product was 75% by mass and the weight-average molecular weight was 40,000. As a result of neutralization titration with hydrochloric acid using methanol as a solvent, it was found that about 20 mol % of the amino group remained. This adhesive polymer had a maximum tensile shearing load of 8.6 N as measured according to JIS K6850.

Further, the measurement results of the maximum tensile shearing load of commercially available adhesive polymers are shown in Table 1.

TABLE 1

| Raw Material Name (Manufacturer Name) | Polymer Name | Maximum Tensile Shearing Load (N) |
|---|---|---|
| Kollidon 90F | polyvinylpyrrolidone | 54.6 |
| Synthesis Example 1 | poly(N-propionylethyleneimine)-modified silicone | 8.6 |
| Baycusan C2000 (COVESTRO AG) | polyurethane-64 | 48.2 |
| PEG 20000 | polyethylene glycol (molecular weight: 20,000) | 3.4 |
| Amphomer 28-4910 (Akzo Nobel N.V.) | (octylacrylamide/acrylate/butylaminoethyl methacrylate) copolymer | 20.5 |
| Amphomer LV-71 (Akzo Nobel N.V.) | (octylacrylamide/hydroxypropyl acrylate/butylaminoethyl methacrylate) copolymer | 32.3 |
| Amphomer HC (Akzo Nobel N.V.) | (alkyl acrylate-octylacrylamide) copolymer | 9.7 |
| Resyn 28-2930 (Akzo Nobel N.V.) | (VA/crotonic acid/vinyl neodecanoate) copolymer | 65.7 |
| Gantrez ES425 (Ashland Inc.) | (vinyl methyl ether/butyl maleate) copolymer | 25.0 |
| Omnirez 2000 (Ashland Inc.) | (vinyl methyl ether/ethyl maleate) copolymer | 34.7 |
| Yodosol GH34F (Akzo Nobel N.V.) | alkyl acrylate copolymer ammonium | 40.5 |
| Yodosol GH800F (Akzo Nobel N.V.) | alkyl acrylate copolymer ammonium | 27.3 |
| Diaformer Z651 (Mitsubishi Chemical Corp.) | (acrylate/lauryl acrylate/stearyl acrylate/ethyl methacrylate amine oxide) copolymer | 80.7 |
| Yukaformer 301 (Mitsubishi Chemical Corp.) | (methacryloyloxyethylcarboxybetaine/alkyl methacrylate) copolymer | 34.0 |
| Yukaformer 104D (Mitsubishi Chemical Corp.) | (methacryloyloxyethylcarboxybetaine/alkyl methacrylate) copolymer | 64.0 |
| Yukaformer 202 (Mitsubishi Chemical Corp.) | (methacryloyloxyethylcarboxybetaine/alkyl methacrylate) copolymer | 79.6 |
| Yukaformer SM (Mitsubishi Chemical Corp.) | (methacryloyloxyethylcarboxybetaine/alkyl methacrylate) copolymer | 57.4 |
| Yukaformer R205S (Mitsubishi Chemical Corp.) | (methacryloyloxyethylcarboxybetaine/alkyl methacrylate) copolymer | 41.1 |
| Baycusan C1004 (COVESTRO AG) | Polyurethane-35 | 66.9 |
| Daitosol 5000SJ (Daito Kasei Kogyo Co., Ltd.) | acrylates/ethylhexyl acrylate copolymer | 29.4 |

[Test 1]

(1) Preparation of Spraying Compositions

Compositions shown in Table 2 or 3 were used as the spraying compositions.

(2) Preparation of Compositions Y

Liquid agents (compositions Y) shown in Tables 4 to 8 were used as the compositions Y.

(3) Decoration of a Skin (Placing of a Solid Material)

Figure 3:
FIG. 3 is a schematic view showing the state that wearable coatings by Examples of the present invention are applied.

A heart-shaped metal film (Confetti Project Wedding Assort 148-1514) was used as the decoration of a skin. As illustrated in FIG. 3, two decorations were mounted at an interval of 1 cm on a skin of the back of a hand by a finger.

(4) Evaluation Methods

In the order shown in Table 10, coatings on the skin surface after the treatment of the skin surface were evaluated for the followability to movements of the skin, the degree of unconspicuousness of the edge, the degree of no uncomfortable feeling, the tolerance to wetting with water, the scratch resistance, and the degree of ease of peeling.

Here, electrostatic spraying will be described.

By using an electrostatic spray apparatus 10 having a constitution shown in FIG. 1 and having an appearance illustrated in FIG. 2, an electrostatic spray method was carried out toward a skin for 60 s. The condition of the electrostatic spray method was as follows.

Applied voltage: 10 kV
Distance between a nozzle and the skin: 100 mm
Amount of a spraying composition discharged: 5 mL/h
Environment: 25° C., 50% RH By carrying out the electrostatic spraying for 20 s, a porous coating composed of a deposit of fibers was formed on a skin of the back of a hand. The coating was applied in a circle of 5 cm in diameter.

(5) Preparation of an ES Sheet

Figure 4:
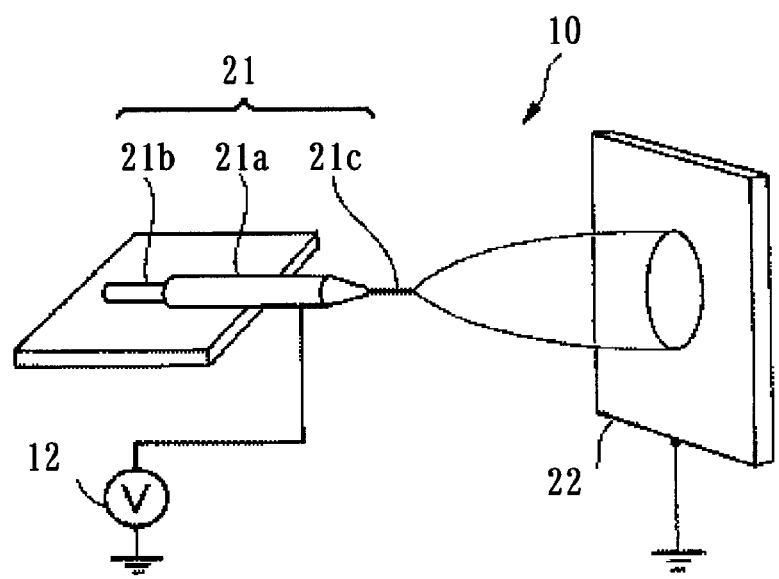
FIG. 4 is a schematic view showing an apparatus carrying out electrostatic spraying on a substrate, in the present invention.

By using an electrostatic spray apparatus having a constitution shown in FIG. 4, an ES sheet was fabricated. As a solution for the ES sheet, a composition indicated in Table 6 was used. The area was made to be 3 cm×3 cm and the basis weight was made to be 1 mg/cm$^2$. The condition of the electrostatic apparatus was as follows.

Voltage: 30 kV
Distance: 200 mm
Discharge amount: 2 mL/h
Environment: 24° C., 40% RH (6) Comparative Example: a Tape A tape used was a Scotch mending tape (width: 12 mm) 810-1-12D, manufactured by 3M Co. The tape was cut into a size of 7.4 cm×1.2 cm, and affixed on the skin to thereby cover the decoration.

(Evaluations)

(1) Followability

The operation of unfolding the fingers of a hand and grasping the hand was repeated two times and lifting of the coating at the grasping thereof was visually evaluated.

Evaluation Criteria
1: The coating lifted at bending of the hand.
2: The coating slightly lifted at the bending.
3: The coating did not lift even at the bending.

(2) Degree of Unconspicuousness of the Edge

The state of the edge of the coating before the fingers of the hand were moved (at still standing) was visually evaluated.

Evaluation Criteria
1: The edge was recognized in the static state.
2: The edge was slightly recognized in the static state.
3: The edge was not recognized.

(3) Degree of No Uncomfortable Feeling

The sensory evaluation was carried out for the uncomfortable feeling before the fingers of the hand were moved (at still standing). The evaluation was carried out by three panelists and determined by consultation thereof.

Evaluation Criteria
1: Strong uncomfortable feeling was felt in the static state.
2: Slight uncomfortable feeling was felt in the static state.
3: No uncomfortable feeling was felt.

(4) Tolerance to Wetting with Water

The tolerance to exposure for 5 s to a flow of a city water was visually evaluated.

Evaluation Criteria
1: The coating came off due to wetting.
2: The coating partially came off due to wetting.
3: The coating did not come off even due to wetting.

(5) Scratch Resistance

The state of the coating when a micro-vibrational load was exerted from on the decoration by a finger was visually evaluated.

Evaluation Criteria
1: The decoration came off and the coating was broken.
2: The decoration moved and kinks and the like of the coating were caused.
3: No change occurred in the decoration and no fraying or breakage occurred in the coating.

(6) Degree of Ease of Peeling

The peelability of the decoration when the coating was peeled was visually evaluated.

Evaluation Criteria
1: When the coating was peeled, the entirety of the decoration remained on the skin.
2: When the coating was peeled, a part of the decoration remained.
3: When the coating was peeled, also the entirety of the decoration was peeled.

[Test 2]

(1) Preparation of Spraying Compositions

Spraying compositions used were composition in Table 2.

(2) Preparation of Compositions Y

Liquid agents (compositions Y1) in Table 4 were used.

(3) Painting on a Skin

For painting on a skin, an air brush was used. A coating material used for the air brush was Vibe (blue) manufactured by European Body Art, and a picture of a butterfly of about 4 cm in diameter was drawn by using a stencil. A compressor used was a Minimarukun AC-100 manufactured by G-too Co., Ltd. The drawing was carried out by using the air brush RB-2 manufactured by Rich Co. The difference ΔE between before painting and after painting is shown in Table 12.

(4) Tattoo Seal

A Tattoo Seal White EJP-TATHW manufactured by Elecom Co. was used. A picture was drawn on the tattoo seal by using the air brush as in the painting on a skin, and the seal was transferred to a skin surface according to its instruction.

(5) Evaluation Methods

In the order in Table 11, after a skin surface of the inner side of a lower thigh was treated, the coating on the skin surface was evaluated for the followability to movements, the degree of unconspicuousness of the edge, the degree of no uncomfortable feeling, and the transferability to the skin.

Here, electrostatic spraying will be described.

By using an electrostatic spray apparatus 10 having a constitution shown in FIG. 1 and having an appearance illustrated in FIG. 2, an electrostatic spray method was carried out toward a skin for 60 s. The condition of the electrostatic spray method was as follows.

Applied voltage: 10 kV
Distance between a nozzle and the skin: 100 mm
Amount of a spraying composition discharged: 5 mL/h
Environment: 25° C., 50% RH By carrying out the electrostatic spraying for 2 min, a porous coating composed of a deposit of fibers was formed on a skin surface of the back of a hand. The coating was applied in the shape of a 5-cm×5-cm square.

(Evaluations)

(1) Followability

Lifting of the coating when the skin was moved was visually evaluated.

Evaluation Criteria

1: When the skin was moved, the coating was peeled.

2: When the skin was moved, wrinkling occurred on the coating.

3: Even when the skin was moved, no peeling or wrinkling occurred on the coating.

(2) Degree of Unconspicuousness of the Edge

The state of the edge at still standing was visually evaluated.

Evaluation Criteria

1: The edge was recognized in the static state.

2: The edge was slightly recognized in the static state.

3: The edge was not recognized.

(3) Degree of No Uncomfortable Feeling

The sensory evaluation was carried out for the uncomfortable feeling in the static state.

Evaluation Criteria

1: Strong uncomfortable feeling was perceived in the static state.

2: Slight uncomfortable feeling was perceived in the static state.

3: No uncomfortable feeling was perceived.

(4) Transferrability to a Skin Surface

The degree of transfer of the paint to a skin when the coating was peeled was visually evaluated.

Evaluation Criteria

1: When the coating was peeled, the entirety of the paint remained on the skin.

2: When the coating was peeled, a part of the paint remained on the skin.

3: When the coating was peeled, the paint did not remain at all.

TABLE 2

| | Component | Composition X (mass %) |
|---|---|---|
| (a) | ethanol | 80.3 |
| (a) | purified water | 0.4 |
| (b) | polyvinyl butyral (*1) | 12.0 |
| | 1,3-butylene glycol | 6.8 |
| | distearyldimonium chloride | 0.5 |
| | Total | 100.0 |

(*1): S-Lec B BM-1 (Sekisui Chemical Co., Ltd.)

TABLE 3

| Component | Composition X2 (mass %) |
|---|---|
| ethanol | 86.1 |
| purified water | 0.4 |
| polyvinyl butyral (*2) | 6 |
| 1,3-butylene glycol | 7.5 |
| Total | 100.0 |

(*2): Mowital B 75H (Kuraray Co., Ltd.)

TABLE 4

| | Component | Composition Y1 mass % |
|---|---|---|
| (e) | glycerol | 10.00 |
| (c) | (octylacrylamide/acrylic acid/butylaminoethyl methacrylate) copolymer (*3) | 7.00 |
| (c) | (C10-30) alkyl acrylate acrylic acid copolymer (*4) | 0.60 |
| (d) | liquid paraffin | 5.00 |
| (d) | cetearyl alcohol | 0.50 |
| | Laureth-3 | 0.25 |
| | Ceteareth-20 (*5) | 0.25 |
| | 2-amino-2-methyl-1-propanol | 1.10 |
| | phenoxyethanol | 0.15 |
| | sodium hydroxide | 0.05 |
| (d) | methyl paraoxybenzoate | 0.20 |
| (d) | ethyl paraoxybenzoate | 0.10 |
| | purified water | 74.80 |
| | Total Amount | 100.00 |

(*3): Amphomer 28-4910 (Akzo Nobel N.V.)
(*4): Pemulen TR-1 (Lubrizol Advanced Materials, Inc.)
(*5): Eumulgin B-2 (BASF AG)

TABLE 5

| | Component | Composition Y2 mass % |
|---|---|---|
| (e) | glycerol | 4.00 |
| (d) | stearyl alcohol | 4.00 |
| (d) | cetyl alcohol | 1.00 |
| (d) | cetyl ester | 1.30 |
| | polyoxyethylene cetostearyl ether | 0.75 |
| (d) | dimethylpolysiloxane (200 cst) | 0.50 |
| (d) | isopropyl myristate | 0.50 |
| | Sepigel (*6) | 0.30 |
| | fragrance | 0.01 |
| | plant extract | 0.50 |
| (d) | glyceryl distearate | 0.12 |
| (d) | glyceryl monostearate | 0.12 |
| (d) | methyl parabenzoate | 0.20 |
| (d) | propyl parabenzoate | 0.10 |
| | purified water | 86.60 |
| | Total | 100.00 |

(*6): polyacrylamide/(C13, C14)isoparaffin/laureth-7 (Seppic Co., Sepigel 305)

TABLE 6

| | Component | Composition Y3 mass % |
|---|---|---|
| (e) | glycerol | 14.00 |
| (e) | propanediol | 3.00 |
| (e) | 1,3-butylene glycol | 3.00 |
| (e) | polyethylene glycol (1540-G) | 3.00 |
| (d) | neopentyl glycol dicaprate | 2.00 |
| (d) | olive oil | 2.00 |
| (d) | squalane | 2.00 |
| (d) | glyceryl behenate | 2.00 |
| (d) | petroleum | 1.00 |
| (d) | cetanol | 1.00 |
| (d) | dimethylpolysiloxane | 0.30 |
| (d) | methylpolysiloxane | 5.00 |
| (c) | carboxyvinyl polymer (*7) | 0.20 |
| (c) | xanthan gum | 0.05 |
| | polyglyceryl-2 diisostearate (*8) | 0.35 |

TABLE 6-continued

| Component | Composition Y3 mass % |
|---|---|
| N-stearoyl-L-glutamic acid | 0.60 |
| plant extract | 1.50 |
| fragrance | 0.30 |
| arginine | 0.35 |
| sodium hydroxide | 0.10 |
| purified water | 58.25 |
| Total | 100.00 |

(*7): Carbopol 981 (Lubrizol Advanced Materials, Inc.)
(*8): Cosmol 42V (Nisshin Oillio Group, Ltd.)

TABLE 7

| | Component | Composition Y4 mass % |
|---|---|---|
| (d) | liquid paraffin | 59.8 |
| (d) | glyceryl tri(caprylate/caprate) | 20.0 |
| (d) | isopropyl myristate | 20.0 |
| (d) | safflower oil | 0.1 |
| | fragrance | 0.1 |
| Total | | 100.0 |

TABLE 8

| Component | Composition Y5 (mass %) |
|---|---|
| water | 72.9 |
| glycerol | 10 |
| polyurethane resin | 17.1 |

TABLE 9

| Component | ES sheet mass % |
|---|---|
| ethanol | 84.6 |
| purified water | 0.4 |
| polyvinyl butyral BM-1 (Sekisui Chemical Co., Ltd.) | 12.0 |
| di(phytosteryl/octyldodecyl) lauroylglutamate (*10) | 3.0 |
| Total | 100.0 |

(*10): Eldew PS203 (Ajinomoto Co., Inc.)

TABLE 10

| | Example 1 | Example 2 | Example 3 | Example 4 | Example 5 | Example 6 | Example 7 | Example 8 | Example 9 | Example 10 | Example 11 | Comparative Example 1 | Comparative Example 2 |
|---|---|---|---|---|---|---|---|---|---|---|---|---|---|
| 1st | composition X | composition Y1 | decoration | composition Y1 | decoration | decoration | decoration | composition Y1 | composition Y1 | composition Y5 | composition Y1 | decoration | composition Y1 |
| 2nd | composition Y1 | composition X | composition X | decoration | composition X | composition X | composition X | decoration | composition X | composition X | composition X2 | tape | decoration |
| 3rd | decoration | decoration | composition Y1 | composition X | composition Y2 | composition Y3 | composition Y4 | ES sheet | decoration | decoration | Glitter | — | — |
| 4th | composition X | composition X | — | — | — | — | — | composition Y2 | composition Y2 | composition X | composition X2 | — | — |
| 5th | composition Y2 | composition Y2 | — | — | — | — | — | — | composition Y2 | composition Y2 | composition Y2 | — | — |
| Evaluation | | | | | | | | | | | | | |
| Followability | 3 | 3 | 3 | 3 | 2 | 3 | 3 | 2 | 3 | 3 | 3 | 1 | N.D. (no coating) |
| Degree of unconspicuousness of edge of coating | 3 | 3 | 3 | 3 | 3 | 3 | 3 | 2 | 3 | 3 | 3 | 1 | N.D. (no coating) |
| Degree of no uncomfortable feeling | 3 | 3 | 3 | 3 | 3 | 3 | 3 | 3 | 3 | 3 | 3 | 1 | 3 |
| In wetting | 3 | 3 | 3 | 3 | 3 | 3 | 3 | 3 | 3 | 3 | 3 | 3 | 1 |
| Scratch resistance | 3 | 3 | 3 | 2 | 2 | 2 | 2 | 2 | 3 | 3 | 3 | 3 | 1 |
| Peelability of decoration | 3 | 3 | 2 | 2 | 2 | 1 | 3 | 2 | 3 | 3 | 3 | 3 | N.D. (no coating) |

TABLE 11

|  | Example 1 | Comparative Example 1 | Comparative Example 2 |
|---|---|---|---|
| 1st | composition Y1 | tattoo seal | Air brush |
| 2nd | composition X | Air brush | — |
| 3rd | composition Y1 | — | — |
| 4th | Air brush | — | — |
| Evaluations |  |  |  |
| Followability | 3 | 2 | N.D. (no coating) |
| Degree of unconspicuousness of edge | 3 | 1 | N.D. (no coating) |
| Degree of no uncomfortable feeling | 3 | 3 | 3 |
| Transferrability to skin | 3 | 3 | 1 |

TABLE 12

|  | Skin | Reaction after painting with air brush | ΔE |
|---|---|---|---|
| L* | 68.70 | 30.75 | 56.47 |
| a* | 7.12 | −1.64 |  |
| b* | 15.69 | −25.20 |  |

REFERENCE SIGNS LIST

10 ELECTROSTATIC SPRAY APPARATUS
11 LOW-VOLTAGE POWER SOURCE
12 HIGH-VOLTAGE POWER SOURCE
13 AUXILIARY ELECTRIC CIRCUIT
14 PUMP MECHANISM
15 CONTAINER
16 NOZZLE
17 PIPE
18 FLEXIBLE PIPE
19 CURRENT LIMITING RESISTANCE
20 HOUSING
21 SYRINGE
21a CYLINDER
21b PISTON
21c CAPILLARY
22 ELECTROCONDUCTIVE COLLECTOR

The invention claimed is:

1. A method for producing a wearable coating having one or more solid materials fixed on skin, the method comprising:
   placing one or more solid materials on a skin surface, wherein the minimum dimension of at least one side of said one or more solid materials is >1 mm;
   after said placing, affixing a nanofiber sheet on the skin surface; and, after said affixing or before said placing, applying to the skin a composition Y, comprising one or more components selected from the group consisting of 0.5% to 15% of an adhesive polymer; and
   an oil.

2. The method according to claim 1, wherein said placing comprises placing the one or more solid materials discontinuously on the skin surface.

3. The method according to claim 1, wherein said placing comprises placing the one or more solid materials on the skin surface by spraying or mounting.

4. The method according to claim 1, wherein the composition Y comprises an adhesive polymer.

5. The method according to claim 1, wherein the composition Y comprises an adhesive polymer and an oil.

6. The method according to claim 1, wherein the adhesive in the composition Y is an adhesive polymer having a maximum tensile shear load of 1 N or more.

7. The method according to claim 1, wherein said applying comprises applying the composition Y to the skin by using a device other than an electrostatic spray device.

8. The method according to claim 2, wherein the composition Y further comprises a polyol.

9. A method for producing a wearable coating having one or more solid materials fixed on skin, the method comprising:
   placing one or more solid materials on a skin surface, wherein the minimum dimension of at least one side of said one or more solid materials is >1 mm;
   after said placing, affixing a nanofiber sheet on the skin surface; and, after said affixing or before said placing, applying a composition Y to the skin, comprising one or more components selected from the group consisting of an adhesive polymer having a maximum tensile shearing load measured by JIS K6850 of 1N or more; and
   an oil.

10. The method according to claim 9, wherein said placing comprises placing the one or more solid materials discontinuously on the skin surface.

11. The method according to claim 9, wherein said placing comprises placing the one or more solid materials on the skin surface by spraying or mounting.

12. The method according to claim 9, wherein the composition Y comprises an adhesive polymer.

13. The method according to claim 9, wherein the composition Y comprises an adhesive polymer and an oil.

14. The method according to claim 9, wherein said applying comprises applying the composition Y to the skin by using a device other than an electrostatic spray device.

15. The method according to claim 9, wherein the composition Y further comprises a polyol.

* * * * *